US010139460B2

United States Patent
Panther et al.

(10) Patent No.: US 10,139,460 B2
(45) Date of Patent: Nov. 27, 2018

(54) SYSTEM AND METHOD FOR DELTA RELAXATION ENHANCED MAGNETIC RESONANCE IMAGING

(71) Applicant: SYNAPTIVE MEDICAL (BARBADOS) INC., Bridgetown (BB)

(72) Inventors: Alexander Gyles Panther, Toronto (CA); Cameron Anthony Piron, Toronto (CA); Jeff Alan Stainsby, Toronto (CA); Chad Tyler Harris, Toronto (CA)

(73) Assignee: SYNAPTIVE MEDICAL (BARBADOS) Inc., Bridgetown (BB)

( * ) Notice: Subject to any disclaimer, the term of this patent is extended or adjusted under 35 U.S.C. 154(b) by 0 days.

(21) Appl. No.: 14/902,221

(22) PCT Filed: Feb. 23, 2015

(86) PCT No.: PCT/CA2015/000106
§ 371 (c)(1),
(2) Date: Dec. 30, 2015

(87) PCT Pub. No.: WO2016/134436
PCT Pub. Date: Sep. 1, 2016

(65) Prior Publication Data
US 2017/0293005 A1 Oct. 12, 2017

(51) Int. Cl.
*G01R 33/44* (2006.01)
*A61B 5/00* (2006.01)
(Continued)

(52) U.S. Cl.
CPC .............. *G01R 33/445* (2013.01); *A61B 5/00* (2013.01); *A61B 5/05* (2013.01); *G01R 33/5602* (2013.01); *G01R 33/56518* (2013.01)

(58) Field of Classification Search
CPC .............. G01R 33/445; G01R 33/5602; G01R 33/56518; A61B 5/00; A61B 5/05
See application file for complete search history.

(56) References Cited

U.S. PATENT DOCUMENTS 7,800,367 B2 9/2010 Bhardwaj et al.
2004/0044281 A1* 3/2004 Jesberger .............. A61B 5/0261
600/419

(Continued)

FOREIGN PATENT DOCUMENTS

CA 2717906 A1 9/2009

OTHER PUBLICATIONS

Kato et al. Silent Cerebral Microbleeds on T2*-Weighted MRI: Correlation with Stroke Subtype, Stroke Recurrence, and Leukoaraiosis. (c)2002 American Heart Association: Stroke, vol. 33: 1536-1540.*

(Continued)

*Primary Examiner* — Amanda Lauritzen Moher
(74) *Attorney, Agent, or Firm* — Perry + Currier Inc.

(57) ABSTRACT

A delta-relaxation magnetic resonance imaging (DREMR) system is provided. The system includes a main field magnet and field shifting coils. A main magnetic field with a strength B0 can be generated using the main filed magnet and the strength B0 of the main magnetic field can be varied through the use of the field-shifting coils. The DREMR system can be used to perform signal acquisition based on a pulse sequence for acquiring at least one of T2*-weighted signals imaging; MR spectroscopy signals; saturation imaging signals and MR signals for fingerprinting. The MR signal acquisition can be augmented by varying the strength B0 of the main magnetic field for at least a portion of the pulse sequence used to acquire the MR signal.

8 Claims, 14 Drawing Sheets

(51) Int. Cl.
A61B 5/05 (2006.01)
G01R 33/56 (2006.01)
G01R 33/565 (2006.01)

(56) References Cited

U.S. PATENT DOCUMENTS

| | | | | |
|---|---|---|---|---|
| 2011/0160564 A1* | 6/2011 | Alford | ................ | G01R 33/445 600/410 |
| 2013/0049753 A1* | 2/2013 | Taniguchi | ............. | A61B 5/055 324/309 |
| 2016/0178718 A1* | 6/2016 | Bindseil | ................. | H01F 41/04 324/322 |

OTHER PUBLICATIONS

Araya. "Delta Relaxation Enhanced Magnetic Resonance—Development and Application of a Field-Cycling Contrast Mechanism" (2013). Electronic Thesis and Dissertation Repository. 1242. http://ir.lib.uwo.ca/etd/1242.*

Handler et al. "The Status of Delta Relaxation Enhanced Magnetic Resonance Imaging (dreMR)." Presentation No. T162 Scientific Session 19: Novel MRI Methodology (Co-organized with ISMRM) Sep. 9, 2011. http://www.wmis.org/abstracts/2011/data/papers/T162.html (abstract accessed Oct. 18, 2017).*

J Alford et al, "Delta Relaxation Enhanced MR: Improving Activation—Specificity of Molecular Probes through R1 Dispersion Imaging".

S Ungersma et al, "Magnetic resonance imaging with T1 dispersion contrast", Magn Reson Med, 2006.

D Lurie et al, "Field-cycled PEDRI imaging of free radicals with detection at 450 mT", Magn Reson Imaging, 2005.

Koenig et al, "Magnetic field dependence of 1/T1 of protons in tissue." Investigative Radiology, 1984; and P Rinck et al, "Field-cycling relaxometry: medical applications", Radiology, 1988.

Torheim et al., "Future Extraction and Classification of Dynamic Contrast-Enhanced T2*-Weighted BreastImage Data", IEEE Transactions on Medical Imaging. vol. 20, No. 12, Dec. 2001. pp. 1293-1301.

Chavhan et al. "Principles, Techniques, and Applications of T2*-based MR Imaging and Its Special Applications", RadioGraphics, 2009, 29:1433-1449.

International Search Report, dated Nov. 9, 2015, PCT/CA2015/000106.

* cited by examiner

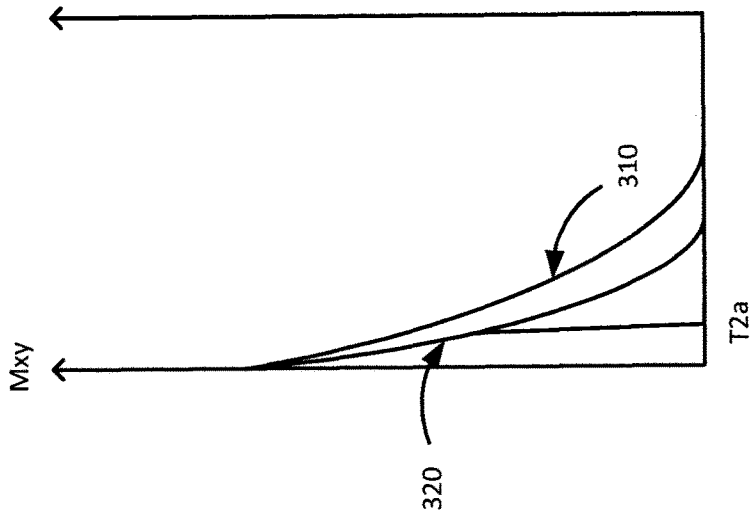
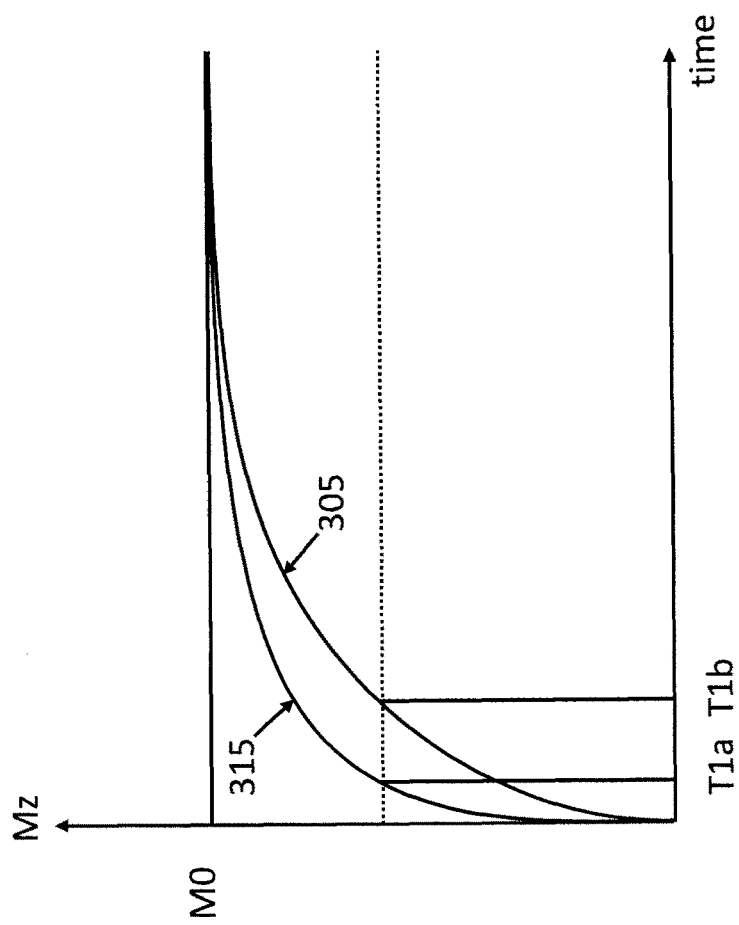
FIG. 3

SYSTEM AND METHOD FOR DELTA RELAXATION ENHANCED MAGNETIC RESONANCE IMAGING

FIELD OF THE INVENTION

The present invention relates generally to magnetic resonance imaging. More specifically, the present invention relates to delta relaxation enhanced magnetic resonance imaging.

BACKGROUND OF THE INVENTION

Magnetic resonance imaging (MRI) is a major imaging technique used in medicine. MRI is capable of generating detailed images of soft tissues such as the brain, muscles and kidneys. Specific properties of the various compounds found inside tissues, such as water and/or fat, are used to generate images. When subjected to a strong magnetic field, the vector sum of the nuclear magnetic moments of a large number of atoms possessing a nuclear spin angular momentum, such as hydrogen, which is abundant in water and fat, will produce a net magnetic moment in alignment with the externally applied field. The resultant net magnetic moment can furthermore precess with a well-defined frequency that is proportional to the applied magnetic field. After excitation by radio frequency pulses, the net magnetization will generate a signal that can be detected.

Delta relaxation enhanced magnetic resonance imaging (DREMR) generally referred to as field-cycled relaxometry or field-cycled imaging is an MRI technique that offers the possibility of using underlying tissue contrast mechanism which vary with the strength of the applied magnetic field to generate novel image contrasts. To achieve DREMR contrast, the main magnetic field is varied as a function of time during specific portions of an MR pulse sequence. A field-shifting electromagnet coil is used to perform the field variation. To date the DREMR imaging methods have focused on the effect of main magnetic field variations on the T1 relaxation characteristic of materials being imaged. This, however, is a limited use of a DREMR system.

SUMMARY OF THE INVENTION

It is an object to provide a novel system and method for an MRI scanning system and method that obviates and mitigates at least one of the above-identified disadvantages of the prior art.

According to one aspect, a method of acquiring magnetic resonance (MR) signals at a delta-relaxation enhanced MR imaging (DREMR) system is provided. According to the method, the DREMR system can generate a main magnetic field with a strength of B0 and an initial pulse sequence for acquiring at least one of: T2*-weighted MR imaging signals; susceptibility weighted imaging (SWI) signals; and saturation imaging signals. The main magnetic field strength can be varied to a strength of B1 during at least one portion of the initial pulse sequence and a first image can be acquired based on the initial pulse sequence.

According to another aspect, a method of acquiring MR signals at a DREMR system is provided. According to the method, the DREMR system can generate a main magnetic field with a strength of B0 and an initial pulse sequence for acquiring MR spectroscopy signals. A first spectroscopy signal can be acquired based on the initial pulse sequence. A repeat pulse sequence for acquiring MR spectroscopy signals can also be generated, the repeat pulse sequence corresponding to the initial pulse sequence. The main magnetic field strength can be varied to a strength of B1 during at least one portion of the repeat pulse sequence. A second spectroscopy signal can be acquired based on the repeat pulse sequence and peaks from the first and the second spectroscopy signals can be identified. The identified peaks can then be correlated.

According to yet another aspect, a method of acquiring MR signals at a DREMR system is provided. According to the method, the DREMR system can generate a main magnetic field with a strength of B0 and an initial pulse sequence for acquiring MR signals for fingerprinting. A first image can be acquired based on the initial pulse sequence. A repeat pulse sequence for acquiring MR fingerprinting signals can be generated, the repeat pulse sequence corresponding to the initial pulse sequence. The main magnetic field strength can be varied to a strength of B1 during at least one portion of the repeat pulse sequence and a second image can be acquired based on the repeat pulse sequence. At least one MR signal property can be measured based on the first and the second images. A tissue type can be identified based on the at least one MR signal property.

According to a further aspect a DREMR system is provided. The system can comprise a main magnet operating to generate a main magnetic field with a strength of B0. The system can further comprise radio frequency coils having a transmit aspect and gradient coils operating to generate an initial pulse sequence for acquiring at least one of: T2*-weighted MR imaging signals; susceptibility weighted imaging (SWI) signals; and saturation imaging signals. The system can also comprise field-shifting magnets operating to vary the main magnetic field strength to a strength of B1 during at least one portion of the initial pulse sequence. The radio frequency coils can have a receive aspect operating to acquire a first image based on the initial pulse sequence.

These, together with other aspects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 3 shows illustrative examples of T1 and T2 relaxation diagrams;

DETAILED DESCRIPTION

Figure 1:
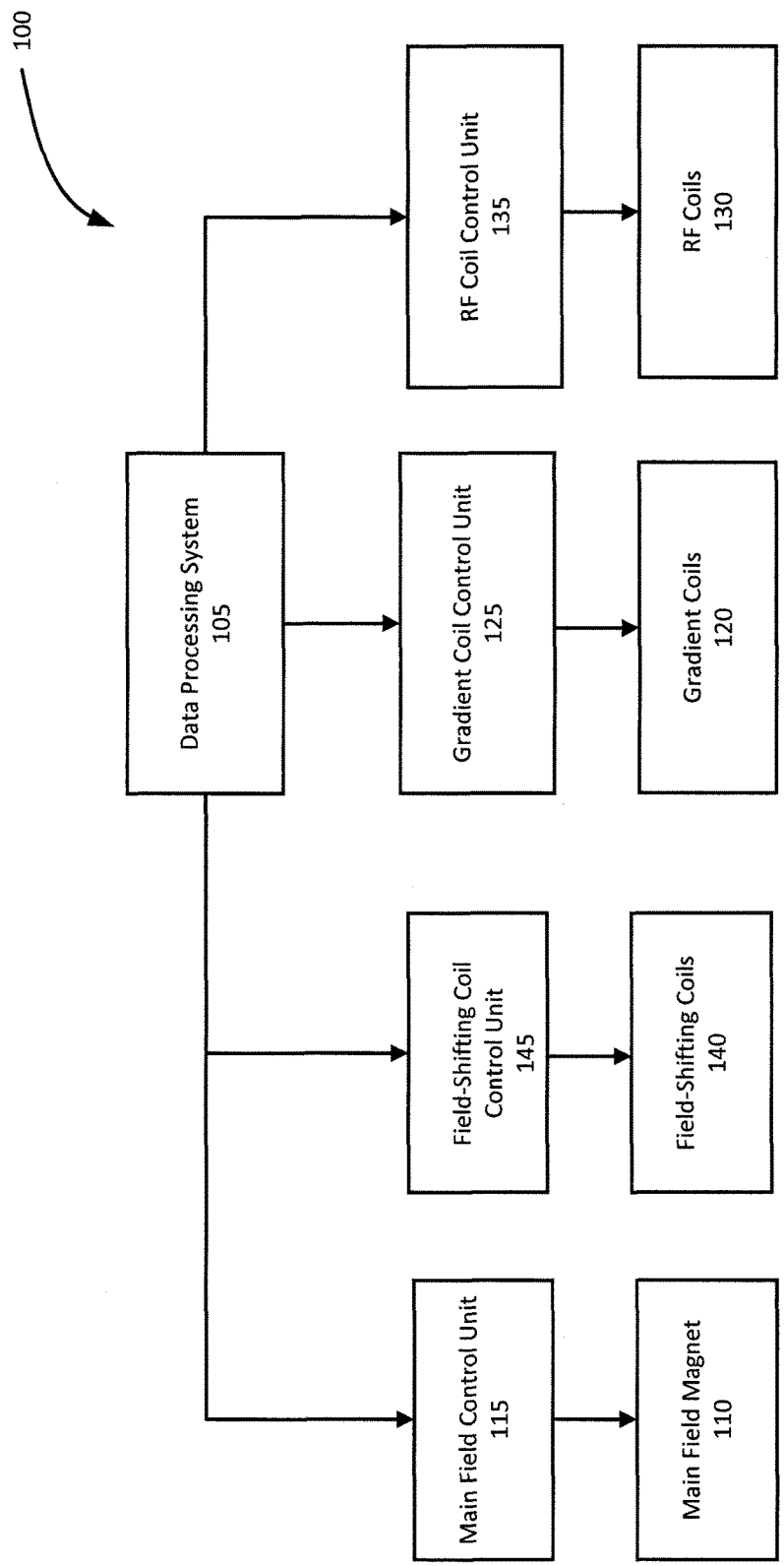
FIG. 1 shows a block diagram of functional subsystems of a delta relaxation magnetic resonance imaging (DREMR) system in accordance with an implementation.

Referring to FIG. 1, a block diagram of a delta relaxation magnetic resonance imaging (DREMR) system, in accordance with an example implementation, is shown at 100. The example implementation of the DREMR system indicated at 100 is for illustrative purposes only, and variations including additional, fewer and/or varied components are possible. Traditional magnetic resonance imaging (MRI) systems represent an imaging modality which is primarily used to construct pictures of magnetic resonance (MR) signals from protons such as hydrogen atoms in an object. In medical MRI, typical signals of interest are MR signals from water and fat, the major hydrogen containing components of tissues. DREMR systems use field-shifting magnetic resonance methods in conjunction with traditional MRI techniques to obtain images with different contrast than is possible with traditional MRI, including molecularly-specific contrast.

As shown in FIG. 1, the illustrative DREMR system 100 comprises a data processing system 105. The data processing system 105 can generally include one or more output devices such as a display, one or more input devices such as a keyboard and a mouse as well as one or more processors connected to a memory having volatile and persistent components. The data processing system 105 can further comprise one or more interfaces adapted for communication and data exchange with the hardware components of MRI system 100 used for performing a scan.

Continuing with FIG. 1, example the DREMR system 100 can also include a main field magnet 110. The main field magnet 110 can be implemented as a permanent, superconducting or a resistive magnet, for example. Other magnet types, including hybrid magnets suitable for use in the DREMR system 100 will now occur to a person of skill and are contemplated. The main field magnet 110 is operable to produce a substantially uniform main magnetic field having a strength B0 and a direction along an axis. The main magnetic field is used to create an imaging volume within which desired atomic nuclei, such as the protons in Hydrogen within water and fat, of an object are magnetically aligned in preparation for a scan. In some implementations, as in this example implementation, a main field control unit 115 in communication with data processing system 105 can be used for controlling the operation of the main field magnet 110.

The DREMR system 100 can further include gradient coils 120 used for encoding spatial information in the main magnetic field along, for example, three perpendicular gradient axis. The size and configuration of the gradient coils 120 can be such that they produce a controlled and uniform linear gradient. For example, three paired orthogonal current-carrying primary coils located within the main field magnet 110 can be designed to produce desired linear-gradient magnetic fields.

In some implementations, the gradient coils 120 may be shielded and include an outer layer of shield coils which can produce a counter magnetic field to counter the gradient magnetic field produced by the primary gradient coils forming a primary-shield coils pair. In such a coil pair the "primary" coils can be responsible for creating the gradient field and the "shield" coils can be responsible for reducing the stray field of the primary coil outside a certain volume such as an imaging volume. The primary-shield coils pair of the gradient coils 120, the primary and shield coils, may be connected in series. It is also possible to have more than two layers of coils for any given gradient axis that together form a shielded gradient coil. Shielded gradient coils 120 may reduce eddy currents and other interference which can cause artefacts in the scanned images. Since eddy currents mainly flow in conducting components of the DREMR system 100 that are caused by magnetic fields outside of the imaging volume (fringe fields), reducing the fringe fields produced by the gradient coils 120 may reduce interference. Accordingly, the shapes and sizes, conductor wire patterns and sizes, and current amplitudes and patterns of the primary-shield coils pair can be selected so that the net magnetic field outside the gradient coils 120 is as close to zero as possible. For cylindrical magnets, for example, the two coils can be arranged in the form of concentric cylinders whereas for vertical field magnets, the two coils may be arranged in coaxial disks.

One side effect of shielding can be that the fields produced by the primary-shield coils pair of the gradient coils 120 may partially cancel each other within the imaging volume. Accordingly, more current can be required to produce a gradient field with a particular strength by shielded gradient coils 120 than by unshielded gradient coils 120. This effect can be quantified as the gradient efficiency, which may be defined as the achievable gradient strength for 1 Ampere of driving current. Another important parameter describing gradient coil performance is called the gradient slew rate, which is the rate of driving a gradient coil from zero to its maximum amplitude. This term is inversely proportional to the inductance of the gradient coil. Typically, in order to increase the efficiency of a shielded gradient coils 120 to be comparable to the efficiency of an unshielded gradient coils 120 the inductance must increase. This increase in inductance will decrease the maximum achievable slew rate. The loss in efficiency for a shielded configuration can depend on the distance and current density ratio between the primary and shield coils. Increasing the distance between the primary-shield coils pair may increase the efficiency.

The conductive components of the gradient coils 120, whether shielded or unshielded and including the primary and shield coils, may consist of an electrical conductor (for example copper, aluminum, etc.). The internal electrical connections can be such that when a voltage difference is applied to the terminals of the gradient coils 120, electric current can flow in the desired path. The conductive components for the three gradient axes for both the primary gradient coils and the gradient shield coils can be insulated by physical separation and/or a non-conductive barrier. The primary gradient windings can be placed on a non-conductive substrate (for example, G 10, FR 4, epoxy or others).

In some variations, the gradient coils 120 may also be provided with thermal control or heat extraction mechanisms. For example, some of the windings can be hollow and coolant can be passed through these hollow conductors to extract heat from the gradient coils 120, produced, for instance, by resistive heating of the windings when electricity is applied. Alternatively, other methods of extracting heat can be used, such as inserting coolant channels within the gradient coils 120. The coolant channels can be in thermal contact with the gradient coil windings. The gradient coils 120 can also be mounted in a thermally-conductive but electrically-non-conductive epoxy to ensure that the mechanical assembly is rigid and to limit the possibility of electrical breakdown.

The magnetic fields produced by the gradient coils 120, in combination and/or sequentially, can be superimposed on the main magnetic field such that selective spatial excitation of objects within the imaging volume can occur. In addition to allowing spatial excitation, the gradient coils 120 can attach spatially specific frequency and phase information to the atomic nuclei placed within the imaging volume, allowing the resultant MR signal to be reconstructed into a useful image. A gradient coil control unit 125 in communication with the data processing system 105 can be used to control the operation of the gradient coils 120.

In some implementations of the DREMR system 100, there may be additional electromagnet coils present, such as shim coils (traditionally, but not limited to, producing magnetic field profiles of 2nd order or higher spherical harmonics) or a uniform field offset coil or any other corrective electromagnet. To perform active shimming (correcting the field distortions that are introduced when different objects are placed within or around the system), the corrective electromagnets, such as the shim coils, carry a current that is used to provide magnetic fields that act to make the main magnetic field more uniform. For example, the fields produced by these coils can aid in the correction of inhomogeneities in the main magnetic field due to imperfections in the main magnet 110, or to the presence of external ferromagnetic objects, or due to susceptibility differences of materials within the imaging region, or any other static or time-varying phenomena.

The DREMR system 100 can further comprise radio frequency (RF) coils 130. The RF coils 130 are used to establish an RF magnetic field with a strength B1 to excite the atomic nuclei or "spins". The RF coils 130 can also detect signals emitted from the "relaxing" spins within the object being imaged. Accordingly, the RF coils 130 can be in the form of separate transmit and receive coils or a combined transmit and receive coil with a switching mechanism for switching between transmit and receive modes.

The RF coils 130 can be implemented as surface coils, which are typically receive only coils and/or volume coils which can be receive and transmit coils. The RF coils 130 can be integrated in the main field magnet 110 bore. Alternatively, the RF coils 130 can be implemented in closer proximity to the object to be scanned, such as a head, and can take a shape that approximates the shape of the object, such as a close-fitting helmet. An RF coil control unit 135 in communication with the data processing system 100 can be used to control the operation of the RF coils 130.

To create a contrast image in accordance with field-shifting techniques, DREMR system 100 can use field-shifting electromagnets 140 while generating and obtaining MR signals. The field-shifting electromagnets 140 can modulate the strength of the main magnetic field. Accordingly, the field-shifting electromagnets 140 can act as auxiliary to the main field magnet 110 by producing a field-shifting magnetic field that augments or perturbs the main magnetic field. A field-shifting electromagnet control unit 145 in communication with the data processing system 100 can be used to control the operation of the field-shifting electromagnets 140.

To reduce interference and artefacts, the field-shifting electromagnets 140 may include a shield similar to the shielded gradient coils 120 described above. The shielded field-shifting electromagnets 140 can have two components: an inner primary field-shifting electromagnets, to produce the field shift and an outer shield field-shifting electromagnets, to form a shield by reducing the stray field of the primary field-shifting electromagnets outside a certain volume such as an imaging volume. Implementing field-shifting primary and shield electromagnets combination that balances the competing needs of low inductance (faster slew rates), high efficiency (greater magnetic field strength for a given current amplitude), and low resistance (less heating and subsequent demands on cooling) is a complex electromagnetic problem.

Indeed, one side effect of shielding the field-shifting electromagnets 140 can be that the fields produced by the primary and shield components of the shielded field-shifting electromagnets 140 may partially cancel each other within the imaging volume. Accordingly, more current can be required to produce a magnetic field with a particular strength by shielded field-shifting electromagnets 140 than by unshielded field-shifting electromagnets 140. This effect can be quantified as the field-shift efficiency, which may be defined as the field-shift amplitude per 1 Ampere of current passing through the electromagnet. The loss in efficiency for a shielded configuration depends on the distance and current density ratio between the shield electromagnets and the primary electromagnets. Increasing the distance between the primary and shield electromagnets may increase the field-shift efficiency.

The conductive components of the field-shifting electromagnets 140, including the primary and shield electromagnets, may consist of an electrical conductor (for example copper, aluminum, etc.). The internal electrical connections can be such that when a voltage difference is applied to the terminals of the field-shifting electromagnets 140, electric current can flow in the desired path. The conductive components for both the primary and the shield electromagnets can be insulated by physical separation and/or a non-conductive barrier. The field-shift windings can be placed in layers on or within a non-conductive substrate (for example, G10, FR4, epoxy or others).

In some variations, the field-shifting electromagnets 140 may also be provided with thermal control or heat extraction mechanisms. For example, where windings are used to form the electromagnets, the windings can be hollow and coolant can be passed through these hollow conductors to extract heat deposited in the electromagnet due to resistive heating of the windings when electricity is applied. Alternatively, other methods of extracting heat can be used, such as inserting coolant channels within the field-shifting electromagnets 140. The coolant channels can be in thermal contact with the field-shifting electromagnets 140. The field-shifting electromagnets 140 can also be mounted in a thermally-conductive but electrically-non-conductive epoxy to ensure that the mechanical assembly is rigid and to limit the possibility of electrical breakdown.

There are many techniques for obtaining images using the DREMR system 100, including T1 and T2 weighted images. To provide a simplified illustration of the DREMR system 100's functionality, simplified operations for obtaining proton density-weighted images are described as a non-limiting example. To create an image in accordance with the example illustration, the DREMR system 100 detects the presence of atomic nuclei containing spin angular momentum in an object, such as those of Hydrogen protons in water or fat found in tissues, by subjecting the object to a relatively large magnetic field. In this example implementation, the main magnetic field has a strength of B0 and the atomic nuclei containing spin angular momentum may be Hydrogen protons or simply protons. The main magnetic field partially polarizes the Hydrogen protons in the object placed in the imaging volume of the main magnet 110. The protons are then excited with appropriately tuned RF radiation, forming an RF magnetic field with a strength of B1, for example. Finally, weak RF radiation signal from the excited protons is detected as an MR signal, as the protons "relax" from the magnetic interaction. The frequency of the detected MR signal is proportional to the magnetic field to which they are subjected. Cross-sections of the object from which to obtain signals can be selected by producing a magnetic field gradient across the object so that magnetic field values of the main magnetic field can be varied along various locations in the object. Given that the signal frequency is proportional to the varied magnetic field created, the variations allow assigning a particular signal frequency and phase to a location in the object. Accordingly, sufficient information can be found in the obtained MR signals to construct a map of the object in terms of proton presence, which is the basis of a traditional MRI image. For example, since proton density varies with the type of tissue, tissue variations can be mapped as image contrast variations after the obtained signals are processed.

Figure 2:
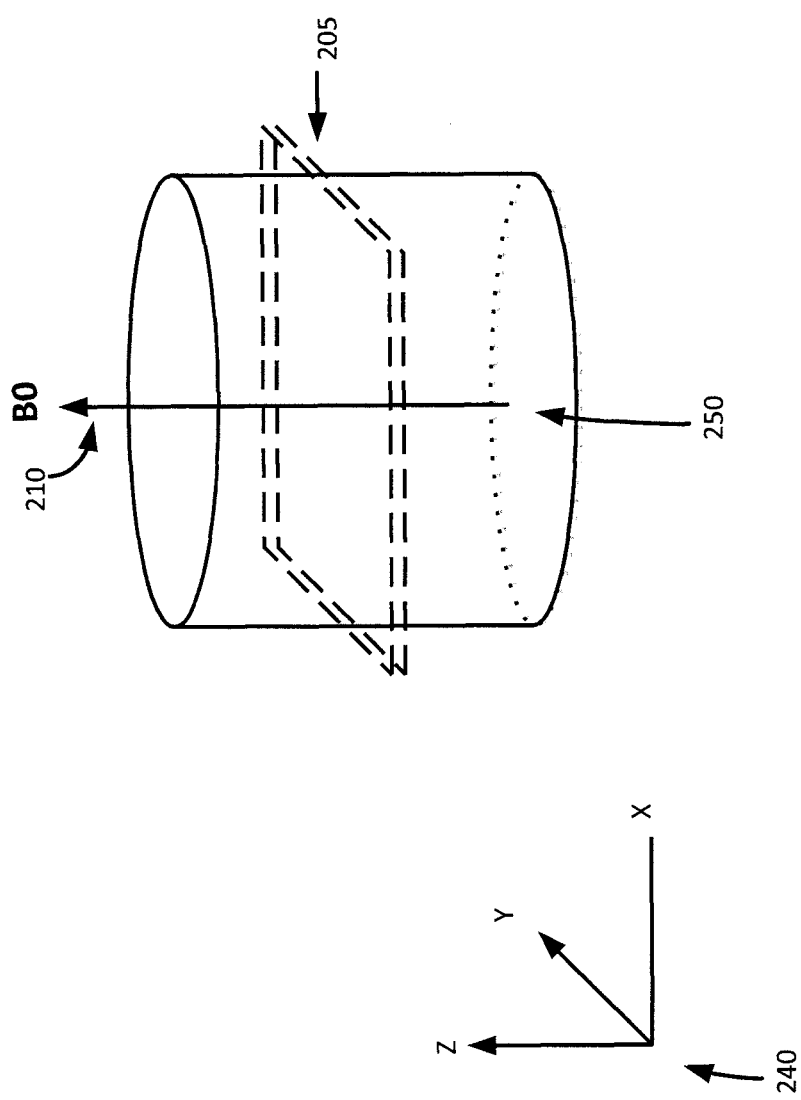
FIG. 2 an imaging volume and corresponding slice to be scanned by the delta relaxation magnetic resonance system of FIG. 1 in accordance with an implementation.

Referring now to FIG. 2, to further illustrate the example signal acquisition process by the DREMR system 100, it will be assumed that an object is placed within an imaging volume 250 of the main magnet 110 having a main magnetic field 210 with a strength B0, pointing along the Z-axis indicated at 240. The object subsequently has a net magnetization vector. In this illustrative example, a slice in a plane along the X and Y axes, as indicated at 205, is being imaged. It should be noted that in this example, the slice has a finite thickness along the Z-axis, creating a volumetric slice 205.

When the object is placed in the main magnetic field B0, the individual spins align themselves in the direction of the Z-axis. Referring to FIG. 3, at equilibrium, the magnetization by main field B0 can produce a net longitudinal magnetization Mz, with an amplitude of M0, parallel with the main magnetic field. Excitation of the spins may be achieved when a radio frequency (RF) pulse that generates the RF magnetic field with an amplitude of B1 is applied at the Larmor frequency, by the RF coils 130. During the application of the RF magnetic field the net magnetization rotates around the applied RF (B1) field and can cause the net magnetization to rotate away from the Z-axis. The component of the rotated magnetization that is projected in the X-Y plane is the net transverse magnetization Mxy. The spins can precess about the applied RF magnetic field until the RF magnetic field is removed.

Once the equilibrium magnetization is perturbed, spin-relaxation processes occur. Spin-lattice relaxation processes cause a return of magnetization to the equilibrium distribution along the Z-axis. Spin-lattice relaxation can thus bring the longitudinal magnetization Mz back toward its maximum value M0, as indicated at 305, with a characteristic time constant T1. A characteristic time representing the recovery of the magnetization along the Z-axis by 37% is called the T1 relaxation time or T1 time. 1/T1 is referred to as the longitudinal relaxation rate.

Spin-spin relaxation, on the other hand, can cause a loss of coherence due to dephasing of the net transverse magnetization. Therefore, during spin-spin relaxation, the transverse magnetization Mxy exponentially decays toward zero, as indicated at 310, with a characteristic time constant T2. A characteristic time representing the decay of the signal by 37%, is called the T2 relaxation time or T2 time. 1/T2 is referred to as the transverse relaxation rate.

Transverse relaxation (T2) can cause irreversible dephasing of the transverse magnetization. There is also a reversible dephasing effect caused by magnetic field inhomogeneities. These additional dephasing fields may arise from a variety of sources including the main magnetic field inhomogeneity, the differences in magnetic susceptibility among various tissues or materials, chemical shift, and gradients applied for spatial encoding. The contribution to the transverse relaxation time from these reversible dephasing effects are typically referred to as T2'. The characteristic relaxation time of the combination of reversible (T2') and irreversible (T2) dephasing effects is typically referred to as T2* relaxation.

The difference between the time constants T1 and T2 are important for development of contrast in MR imaging. The relaxation times can vary with the strength of the magnetic field applied, as well as temperature. Moreover, T1 and T2 values associated with biological tissues can vary. Generally, tissues with shorter T1 times, such as T1a as indicated at 315, can yield greater signal intensity at a given point in time (appearing brighter in images) than those with longer T1 times, such as T1b as indicated at 305, due to the more rapid recovery of signal. On the other hand, tissues possessing short T2 times, such as T2a as indicated at 320, can yield lower signal intensity (appearing darker in images) due to a reduction in the detected transverse magnetization Mxy. The MR signal from an image can be therefore dependent on the combination of the intrinsic tissue properties and extrinsic user-selected imaging parameters and contrast agents.

To obtain images from the DREMR system 100 in the traditional manner, one or more sets of RF pulses and gradient waveforms (collectively called "pulse sequences") are selected at the data processing system 105. The data processing system 105 passes the selected pulse sequence information to the RF control unit 135 and the gradient control unit 125, which collectively generate the associated waveforms and timings for providing a sequence of pulses to perform a scan.

The sequence of RF pulses and gradient waveforms, namely the type of pulse sequence, applied may change which relaxation times have the most influence on the image characteristics. For example, T2* relaxation has a significant influence following a 90° RF pulse which is used in a gradient-echo (GRE) sequence, whereas T2 relaxation has a more significant influence following 90°-180° sequential RF pulses (also known as a spin echo sequence).

Figure 4:
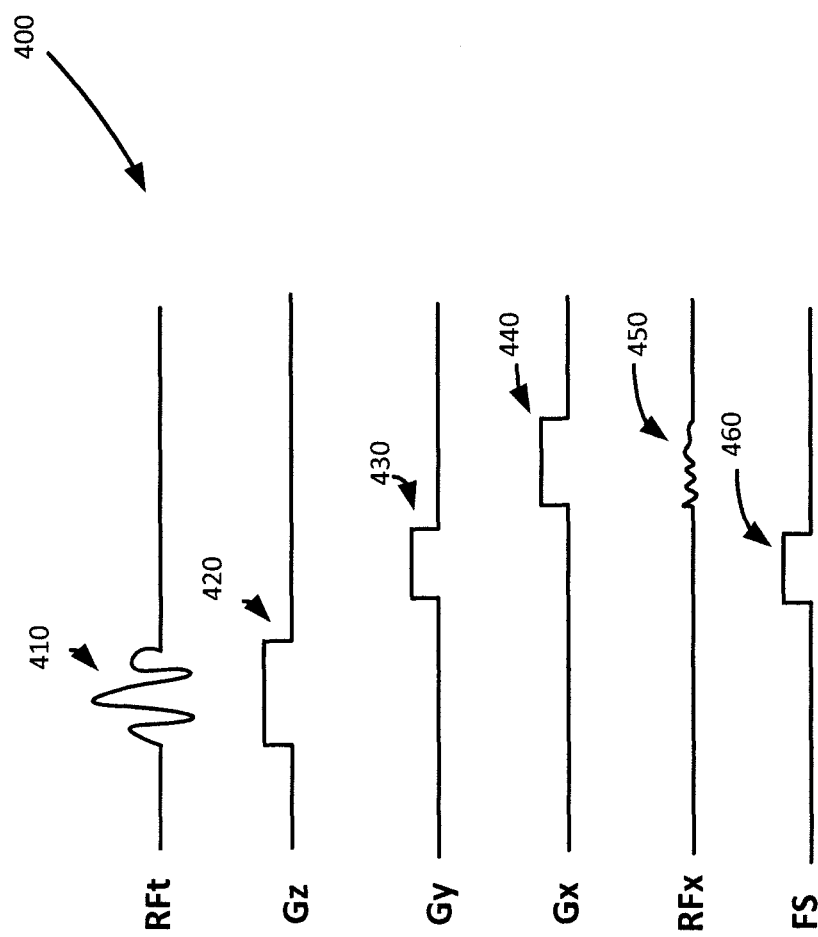
FIG. 4 shows an example pulse sequence in accordance with an implementation.

Referring now to FIG. 4, an illustrative pulse sequence 400 is shown that can be used to acquire images using the DREMR system 100. Specifically, a timing diagram for the example pulse sequence is indicated. The timing diagram shows pulse or signal magnitudes, as a function of time, for transmitted (RFt) signal, magnetic field gradients $G_x$, $G_y$, and $G_z$, received RFx signal and filed-shifting signal (FS). An idealized pulse sequence, simplified for illustrative purposes, can contain a slice selection radio frequency pulse 410 at RFt, a slice selection gradient pulse 420 at Gz, a phase encoding gradient pulse 430 at Gy, a frequency encoding gradient pulse 440 at Gx, as well as a detected MR signal 450 at RFx. The pulses for the three gradients Gx, Gy, and Gz represent the magnitude and duration of the magnetic field gradients that can be generated by the gradient coils 120. The slice selection pulse 410 can be generated by the transmit aspect of RF coils 130. Detected MR signal 450 can be detected by the receive aspect of the RF coils 130. In this illustrative example it will be assumed that transmit aspect and receive aspect of RF coils 130 are formed by distinct coils. Finally, the field-shifting signal FS causes the main magnetic field strength to be changed for the duration of the signal FS. The precise timing, amplitude, shape and duration of the pulses or signals may vary for different imaging techniques. For example, field-shifting signal FS may be applied at a time and manner that allows image contrast to increase for the technique used.

The first event to occur in pulse sequence 400 can be to turn on the slice selection gradient pulse 420. The slice selection RF pulse 410 can be applied at the same time. In this illustrative example, the slice selection RF pulse 410 can be a sinc function shaped burst of RF energy. In other implementations, other RF pulse shapes and durations can be used. Once the slice selection RF pulse 410 is turned off, the slice selection gradient pulse 420 can also be turned off and a phase encoding gradient pulse 430 can be turned on. In some implementations, the field-shifting signal 460 may also be turned on at this point to change the main magnetic field strength. Once the phase encoding gradient pulse 430 is turned off, a frequency encoding gradient pulse 440 can be turned on and a detected MR signal 450 can be recorded. It should be noted that the shapes, magnitudes and durations of the pulses and signals shown in FIG. 4 are chosen for illustrative purposes, and that in implementations, one or more of these factors and others may be varied to achieve the desired scan results. The pulse sequence 400 can be repeated a certain number of times or iterations, typically 256 times, to collect all the data needed to produce one image. The time between each repetition of the pulse sequence 400 can be referred to as the repetition time (TR). Moreover, the duration between the center point of the slice selection pulse 410 and the peak of detected MR signal 450 can be referred to as echo time (TE). Both TR and TE can be varied as appropriate for a desired scan.

To further illustrate the signal acquisition process of DREMR system 100, FIG. 2 is referred to in conjunction with FIG. 4. To select a slice, the slice selection gradient pulse 420 can be applied along the Z-axis, satisfying the resonance condition for the protons located in the slice 205. Indeed, the location of the slice along the Z-axis can be determined based in part on the slice selective gradient pulse 420. Accordingly, the slice selection pulse 410, generated at the same time as the slice selection gradient pulse 420 can excite protons that are located within the slice 205 in this example. Protons located above and below the slice 205 are typically not affected by the slice selection pulse 410.

Continuing with the illustrative example, in accordance with the pulse sequence 400, a phase encoding gradient pulse 430 can be applied after the slice selection gradient pulse 420. Assuming this is applied along the Y-axis, the spins at different locations along the Y-axis can begin to precess at different Larmor frequencies. When the phase encoding gradient pulse 420 is turned off, the net magnetization vectors at different locations can precess at the same rate, but possess different phases. The phases can be determined by the duration and magnitude of the phase encoding gradient pulse 430.

Once the phase encoding gradient pulse 430 is turned off, a frequency encoding gradient pulse 440 can be turned on. In this example the frequency encoding gradient is in the X direction. The frequency encoding gradient can cause protons in the selected slice to precess at rates dependent on their X location. Accordingly, different spatial locations within the slice are now characterized by unique phase angles and precessional frequencies. RF receive coils 130 can be used to receive the detected signal 450 generated by the protons contained in the object being scanned while the frequency encoding gradient pulse 440 is turned on.

Figure 5:
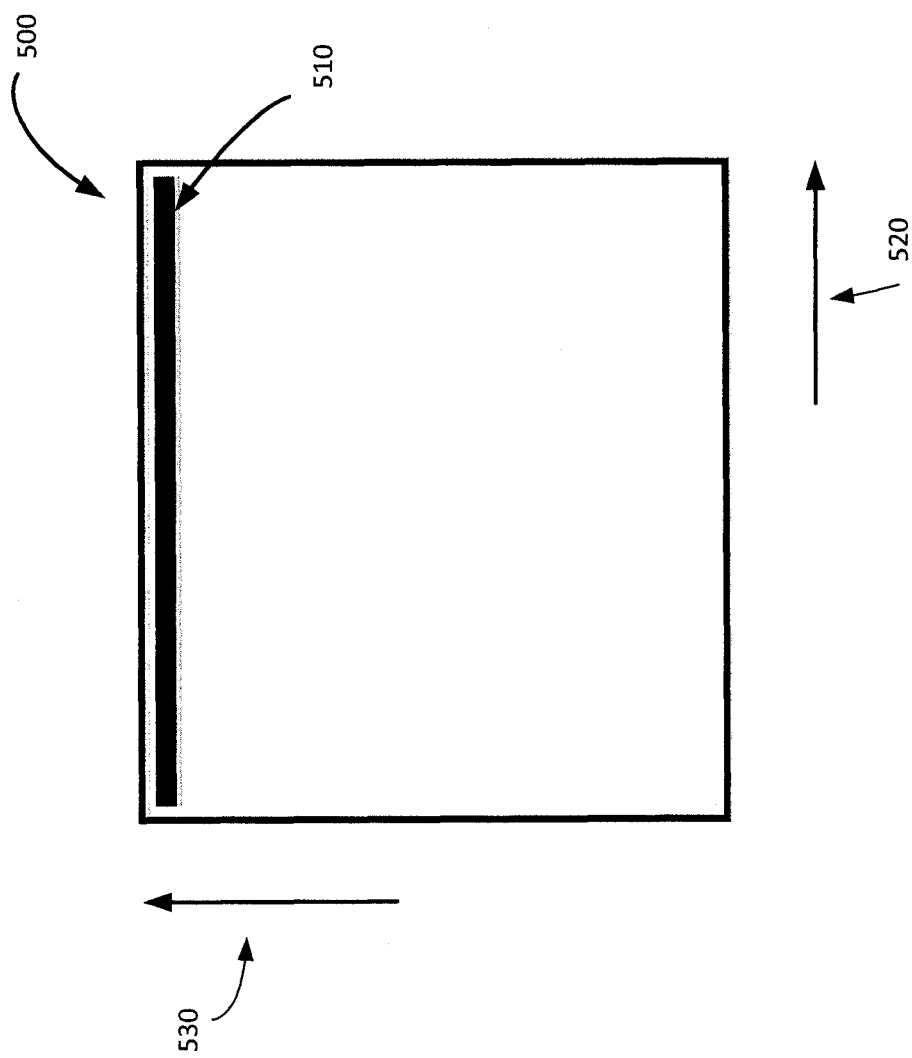
FIG. 5 shows a schematic representation of a k-space containing one received line in accordance with an implementation.

As the pulse sequence 400 is performed by DREMR system 100, the acquired signals can be stored in a temporary matrix referred to as k-space, as shown in FIG. 5 at 500. Typically, k-space is the collection of the detected signals measured for a scan and is in the spatial frequency domain. K-space can be covered by frequency encoding data along the X-axis 520 (Kx) and phase encoding data along the Y-axis 530 (Ky). When all the lines for the k-space matrix for a slice are received (at the end of the scan of a single slice, for example) the data can be mathematically processed, for example through a two-dimensional Fourier-transform, to produce a final image. Thus, k-space can hold raw data before reconstruction of the image into the spatial domain. Typically, k-space has the same number of rows and columns as the final image and is filled with raw data during the scan, usually one line per pulse sequence 400. For example, the first line of k-space 500, indicated at 510, is filled after the completion of the first iteration of the pulse sequence generated for scanning a slice and contains the detected signal for that pulse sequence iteration. After multiple iterations of the pulse sequence, the k-space can be filled. Each iteration of the pulse sequence may be varied slightly, so that signals for the appropriate portions of the k-space are acquired. It should be noted that based on different pulse sequences, other methods of filling the k-space are possible, such as in a spiral manner, and are contemplated.

The choice of specific pulse sequences with optimized parameters can be used by the DREMR system 100 to exploit tissue contrast to obtain images that are able to depict different characteristics of tissue and materials. For example, as mentioned above, T2* relaxation has a significant contribution on relative signal intensities immediately following a 90° RF pulse. T2* relaxation can be one of the main determinants of image contrast with GRE pulse sequences and forms the basis for many magnetic resonance (MR) applications, such as susceptibility-weighted imaging (SWI), perfusion MR imaging, and functional MR imaging. GRE sequences with Tr-based contrast can be used to depict hemorrhage, calcification and iron deposition in various tissues and lesions.

SWI uses phase information in addition to T2* relaxation based contrast to exploit the magnetic susceptibility differences of blood and of iron and calcification in various tissues. Accordingly, SWI is an MR imaging method that takes advantage of signal loss and phase information to allow better imaging of vessels and other tissues.

Functional MRI (fMRI) studies rely on regional differences in cerebral blood flow to delineate regional activity. Blood Oxygenation Level Dependent Imaging (BOLD) is a technique used to generate images in function MRI studies. BOLD-fMRI is able to detect differences in cerebral blood flow in part due to a difference in the paramagnetic properties of oxygenated hemoglobin and deoxygenated hemoglobin. Deoxygenated hemoglobin can be more strongly paramagnetic than oxygenated hemoglobin, and therefore the former can cause greater local dephasing of protons. The local dephasing can reduce the MR signal from the tissues in its immediate vicinity. T2* weighted pulse sequences can be used to detect this change.

The DREMR system 100 can also be used to perform MR spectroscopy. Spectroscopy is the determination of the chemical composition of a substance by observing the spectrum of electromagnetic energy released from a material, including chemical samples, or a tissue sample. MR spectroscopy is a technique whereby MR signals obtained from the nuclei of a material is analyzed to identify the material's composition. MR spectroscopy is based on the fact that components of a material have different resonant frequencies. Rather than displaying MR signals on a gray scale as an image based on the relative signal strength, MR Spectroscopy displays the MR signal as a spectrum graph. Accordingly, the resonance frequency of each compound is represented on a graph as a peak.

MR spectroscopy can be performed with a variety of pulse sequences. A basic sequence consists of a 90 degree RF pulse followed by reception of the MR signal by the receiving components of the RF coils 130, without any intervening gradient pulses. Moreover, many pulse sequences used for imaging, such as a spin echo sequence, can be used for MR spectroscopy as well.

A DREMR system 100 can enhance traditional MR images by modulating or varying the strength B0 of the main magnetic field during at least a portion of one or more pulse sequences. To perform field-shifting scans using a DREMR system 100, magnetic strength level B0 of the main magnetic field may be caused to rapidly, and uniformly change during one or more portions of one or more pulse sequences used to obtain image signals which can form an image. The goal is to cause shifts in the main filed by a predetermined field-shifting magnetic field without causing artifacts or image degradation due to changes in the main magnetic field Specifically, field-shifting electromagnets 140 can be used for obtaining a contrast image by causing a shift in the main magnetic field strength. A field-shifting magnetic field can be applied during a portion of a pulse sequence causing the main magnetic field to be field shifted in strength. More specifically, the static magnetic field strength B0 generated by the main magnet 110 can be either increased or decreased by an amount dB through the use of field-shifting electromagnets 140. The field-shifting magnetic field generated by the field shifting electromagnets 140 may be applied during part, substantially all, or all of a pulse sequence.

Field-shifting properties of DREMR system 100 can be combined with various traditional imaging techniques by modifying traditional pulse sequences as appropriate, and by including an appropriate field-shifting signal, to obtain improved images. For example, in certain types of MR imaging it is often desirable to suppress MR signals arising from different materials. A common example of this is the suppression of MR signals arising from fat while preserving MR signals arising from water. This suppression can be done by making use of the fact that MR signals from different materials may have different frequencies of precession. For example, protons of fat and water have different precessional or Larmor frequencies. Thus, in a homogenous main magnetic field, a sufficiently narrow band RF pulse may be generated by RF coils 130 to excite the desired tissue type only. If such a pulse is used to excite water, for example, in place of the typical slice selection transmission 410, it may primarily tip the magnetization of water molecules into the transverse plane. Hence the resulting MR signal measured will primarily be from the water molecules.

In alternative implementations, a saturation pulse may instead be applied to suppress signals from the unwanted tissue types, such as fat. Thus, a sufficiently narrow band saturation pulse may be used by the DREMR system 100 to tip the protons of the undesired species into the transverse plane. If such a pulse is used to suppress signals from fat protons, for example, then a conventional slice select pulse combination, such as pulse 410 and 420, applied shortly thereafter can primarily tip the magnetization of water protons into the transverse plane since the fat protons would have already been excited by the saturation pulse prior to the application of the slice selection pulse. Because the longitudinal magnetization of fat protons would not have had time to regrow, fat protons would not be available to tip into the transverse plane at the time the slice selection pulse is applied. Thus, the resulting measured MR signal would be primarily obtained from the water protons. The selective RF pulse used to excite the desired species may be referred to as a saturation pulse.

Figure 6:
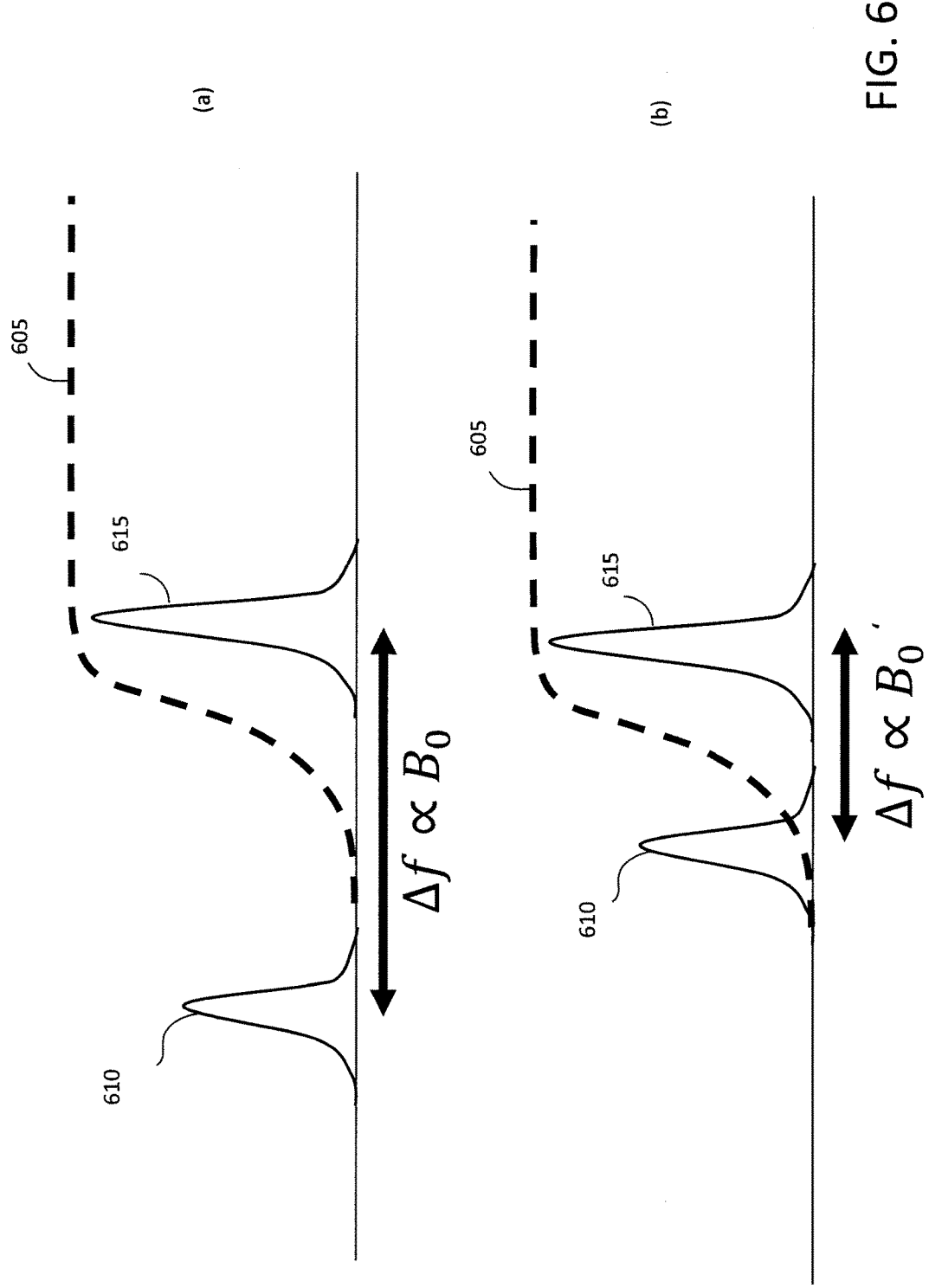
FIG. 6 shows idealized frequency distribution of two materials at different magnetic field strengths.

One difficulty of the saturation method can be that the difference in precessional frequencies between materials is proportional to the main magnetic field strength. At lower main magnetic field strengths, the separation between the precessional frequencies of protons of different materials is lower. For example where B0 is at 0.5T, the separation between precessional frequencies of fat and water protons (whose precessional frequencies differ by 3.5 parts per million), is approximately 70 Hz whereas at 1.5T the separation is approximately 220 Hz. FIG. 6(a) illustrates a generic 15 ms radio frequency saturation pulse response 605 for exciting water, compared to signals from fat (610) and water (615) at one hypothetical main magnetic field strength B0 strength. As illustrated in FIG. 6(b), at a lower strength B0' and a similar duration saturation pulse, the saturation pulse response 605 is not sufficient for robust saturation. It should be noted that illustrations of FIG. 6 are not to scale and the elements have been chosen to clarify the concepts being discussed.

Additional problems involve criteria used for generating narrow band saturation pulses. Saturation pulses which are designed to affect only a narrow range of frequencies are generated in accordance with various practical constraints including how sharply the frequency-dependent effect can occur, how long the RF pulse takes, how much RF power is needed and other criteria. Accordingly, generating effective narrow band saturation pulses get increasingly difficult as the Larmor frequency separation between tissue types decreases.

By applying a field-shifting magnetic field, generated for example, by the field-shifting coils 140, the strength B0 of the main magnetic field can be increased by dB during the spectral selective or saturation portion of the MR pulse sequence. Thus the separation between the precessional frequencies of different materials can be increased, allowing the use of saturation pulses that are more practical and effective. In accordance, a spectrally selective saturation pulse can be designed for a main field strength of B0+dB where dB is the strength added by the magnetic field generated by field-shifting coils 140.

Figure 7:
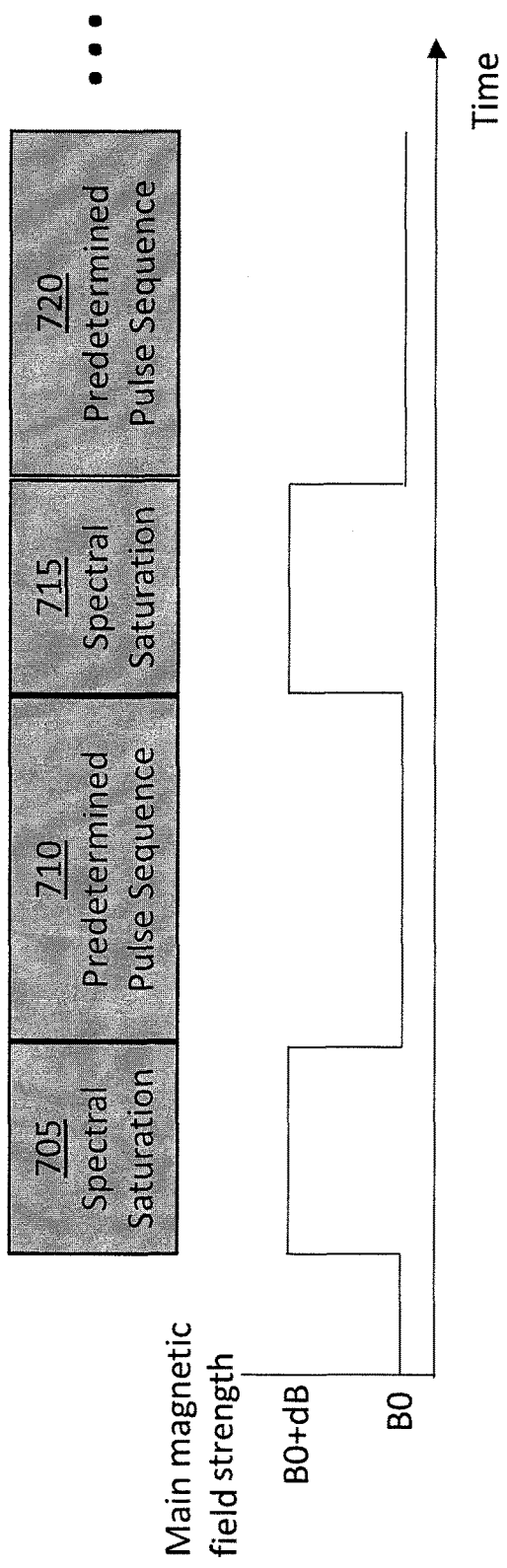
FIG. 7 shows an example pulse sequence for augmented MR signal acquisition using the example DREMR system of FIG. 1 based on spectral suppression.

Referring to FIG. 7, an example method of augmented MR signal acquisition is illustrated. A saturation pulse can be combined with a predetermined pulse sequence, such as pulse 400, to effect MR image acquisition. Accordingly, at 705, the saturation portion of the combined pulse sequence, the saturation pulse is generated by RF coils 130, concurrently with the field-shifting magnetic field, as generated by field-shift coils 140 to increase the main magnetic field strength to B0+dB. The increase, in turn, allows a greater separation of the precession frequencies of different materials, increasing the efficacy of the saturation pulse. After the saturation portion 705, the predetermined portion 710 of the combined pulse sequence is applied. During the predetermined portion 710, the field-shifting field may be turned off and a predetermined pulse sequence such as that of pulse sequence 400 may be applied, the pulse sequence being designed for the main magnetic field strength B0. This process may then be repeated as shown at 715 and 720. The repetition may last as many times as desired to obtain appropriate MR images. In variations, the spectral saturation portion of the combined pulse sequence may not always be provided prior to the beginning of the predetermined pulse sequence. In some variations, the spectral saturation portion may be applied at some point within the predetermined pulse sequence. In further variations, the field-shifting field may also be applied during at least a portion of the predetermined portion 710 of the pulse sequence, the pulse sequence applied being appropriately varied to account for the shifted strength of the main magnetic field. The additional application of the field-shifting field during a pulse sequence portion may be at a different strengths, such as dB1, than the field-shifting field applied during a spectral saturation portion. Moreover, each repetition may involve field-shifting fields that are different in strength and duration than the previous application of the field-shifting field.

Field-shifting properties of DREMR system 100 can also be combined with susceptibility-weighted imaging (SWI). SWI is an MR imaging method where image contrast is generated based on local variations in the magnetic field caused by local magnetic susceptibility variations of materials. SWI uses phase information in addition to T2*-relaxation time based contrast to exploit the magnetic susceptibility differences of tissues and/or materials such as blood and iron. In other words, SWI is an imaging method where image contrast may be enhanced based on magnetic susceptibility differences between tissues and/or materials.

Magnetic susceptibility is a property of material which determines an alteration in a magnetic field caused by a material, when that material is placed in a magnetic field, such as the main magnetic field during MR imaging. For example, the magnetic field strength H inside a tissue, depends on that tissue's magnetic susceptibility which is an inherent property of the tissue. The relationship between the strength H of the susceptibility altered magnetic field and the main magnetic field, B0, can be expressed as $H=(1+X)*B0$ where X is the magnetic susceptibility property of the material. For example, venous blood has a X approximately equal to $-6.56 \times 10^{-6}$ and soft tissues have a X approximately equal to $-9.05 \times 10^{-6}$. Accordingly, SWI imaging can be used to image the difference in susceptibility altered magnetic fields between venous blood and soft tissues as caused by susceptibility difference between the two tissue types.

As an example, venous blood and hemorrhage (bleeds) areas have a susceptibility difference from soft tissue. This difference can cause the venous blood, or hemorrhage areas, to have a signal with a shorter T2* in comparison with soft tissues. Accordingly, signals from venous blood/bleeds can decay away faster and produce less signal in a T2*-weighted pulse sequence (e.g. a GRE sequence).

The strength of the main magnetic field can be another factor that affects the differences in susceptibility altered magnetic field between tissues. Accordingly, increasing the magnetic field applied to an object during imaging through the application of a field-shifting magnetic field, can increase, for example, the imaged contrast between blood such as venous blood and other tissues obtained by SWI imaging. For example, a typical SWI pulse sequence can be generated while the main magnetic field with a strength of B0 is supplemented by the field-shifting magnetic field generated by field electromagnets 140, increasing the main magnetic field strength to B0+dB. The field-shifting magnetic field may be applied during the interval between signal excitation and acquisition.

Figure 8:
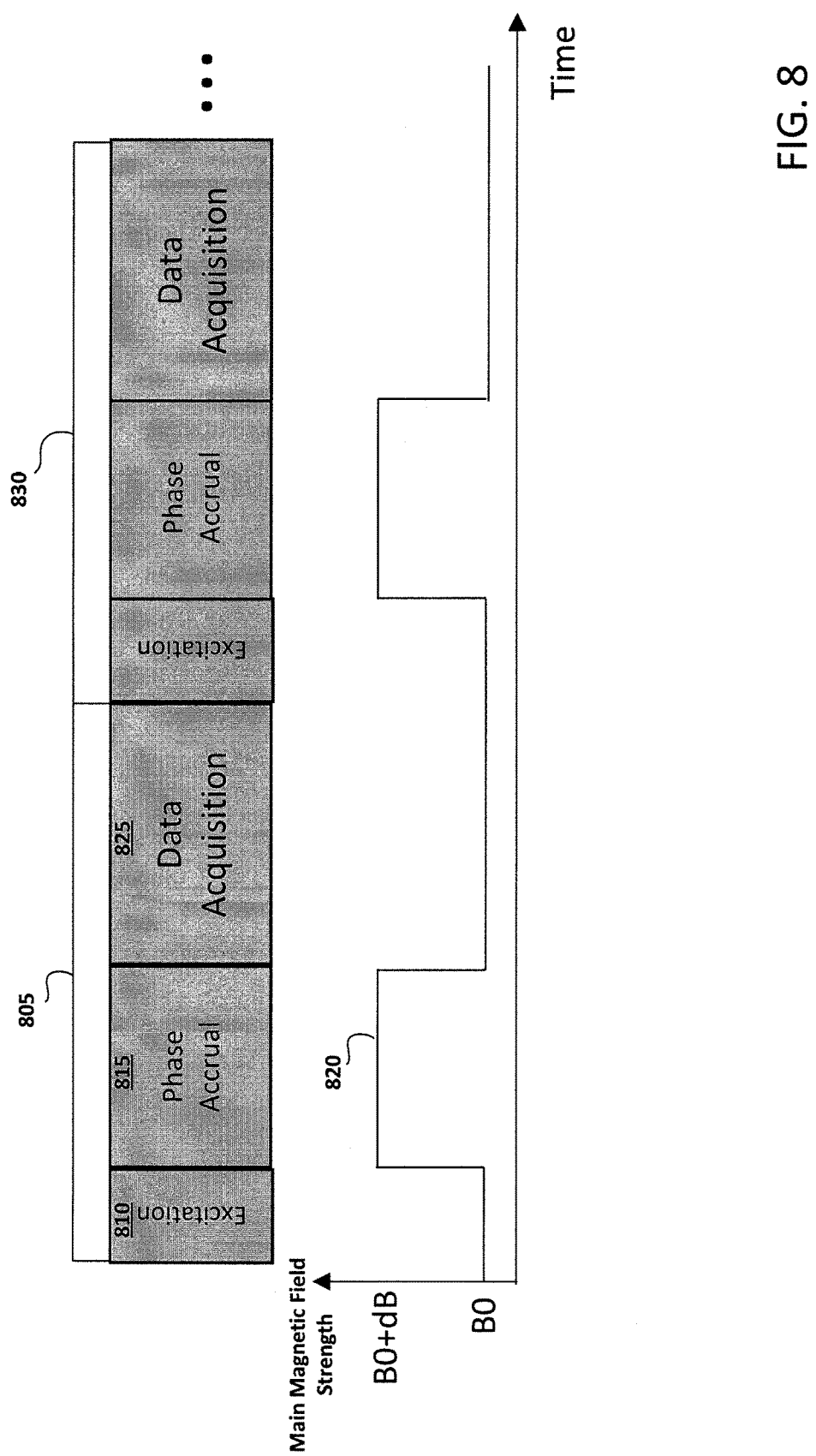
FIG. 8 shows an example pulse sequence for augmented MR signal acquisition using the example DREMR system of FIG. 1 based on susceptibility weighted imaging.

Referring to FIG. 8, an illustrative example method for augmenting SWI with the use of field-shifting magnetic field using the DREMR system 100 is indicated. Excitation is achieved, through application of an RF pulse by the RF coils 130, at an excitation portion 810 of a SWI pulse sequence 805 for acquiring an SWI image. The main magnetic field strength is at B0. At the phase accrual portion 815, of the SWI pulse sequence 805, which is the time during which much of the magnetic-susceptibility-based image contrast is generated, a field-shifting field is applied by the field-shifting coils 140, which causes the strength of the main magnetic field to be increased to B0+dB as indicated at 820. Next, the data acquisition portion 825 of the SWI pulse sequence allows acquisition of the MR signals. The process can be repeated, as indicated at the second SWI pulse sequence 830. The repetition may occur a predetermined number of times to obtain a desired image. It should be noted that a field-shifting magnetic field may be applied during portions of the pulse sequence other than the phase accrual portion and the pulse sequence portions adjusted as desired in accordance with the changed main magnetic field strength. Moreover, the strength and the duration of the field-shifting field applied may vary at different portions or different repetitions of the SWI pulse sequence.

In variations, SWI may be used as a method that can help visualize small bleeds in tissue. In some situations, such as small tissue regions where hemorrhaging has occurred or small areas of blood, detecting the contrast difference due to susceptibility effects can be challenging, especially at lower magnetic field strengths where the susceptibility effect is reduced compared to high fields. In these situations, the reduced variation in signal strength due to the susceptibility effect may be enhanced by combining images with different levels of susceptibility weighting. This can be achieved by acquiring images at different main magnetic field strengths. As an example, for some tissues, the corresponding signal obtained in an SWI image can be high but may not change significantly when the image is acquired using different main magnetic field strengths. Furthermore, there may also be a region of a small bleed (background tissue into which blood has hemorrhaged) for which the corresponding SWI image signal can be low but may change significantly with different main magnetic field strengths. If the small bleed region is embedded within the background tissue, the image contrast between an image location containing background tissue only and an image location containing a region of small bleed would be proportionally small. If two images are acquired at two different magnetic field strengths and the images are subsequently subtracted, the background tissue signal would be eliminated and the relative contrast between the region containing background tissue only and one containing background tissue and a small bleed would be increased.

As an illustrative example, an SWI image can be acquired in accordance with a SWI pulse sequence at a first main magnetic field strength, such as B0. The acquisition can be followed by the acquisition of one or more additional susceptibility weighted images using the same SWI pulse sequence, but at different main magnetic field strengths as achieved through the application of a field-shifting magnetic field by field-shifting coils 140. The images from each of these acquisitions, each image being acquired at a different main magnetic field strength, can then be combined to produce an image that emphasizes regions where the susceptibility-induced contrast varied from image to image based on the variation of the main field strength to field strength. The two images may be combined in any manner that can increase the relative image contrast. This may include subtracting images in pairs; summing all the images together; fitting the signal at each pixel location across the images to some parametric model; or other mathematical combinations.

Figure 9:
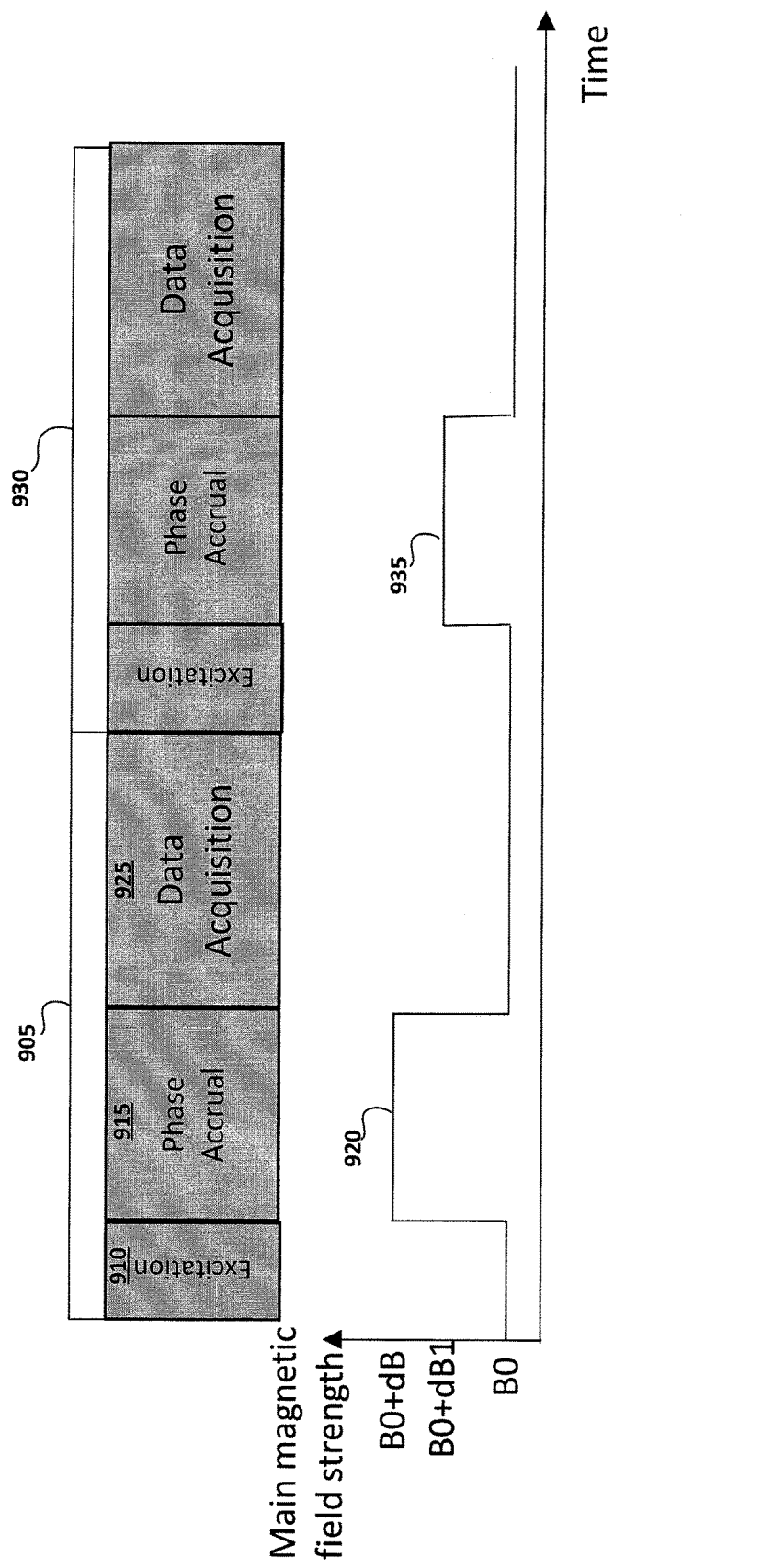
FIG. 9 shows an example pulse sequence for augmented MR signal acquisition using the example DREMR system of FIG. 1 based on susceptibility weighted imaging.

Referring to FIG. 9, a simplified example of a method for visualizing small bleeds in tissues using the DREMR system 100 is illustrated. Excitation can be achieved, through application of an RF pulse by the RF coils 130, at excitation portion 910 of a SWI pulse sequence 905 for acquiring an SWI image. At the phase accrual portion 915, of the SWI pulse sequence 905, which is typically the time during which much of the magnetic-susceptibility-based image contrast can be generated, a field-shifting field can be applied by the field-shifting coils 140, at least during a part of the portion 915. The application of the field-shifting field typically causes the strength of the main magnetic field to be increased to B0+dB as indicated at 920. Next, the data acquisition portion 925 of the SWI pulse sequence can allow the acquisition of the MR signals and thus a portion of an MR image. The process can then be repeated, as indicated at the second SWI pulse sequence 930. However, during the SWI pulse sequence 930, the field-shifting field applied by the field-shifting coils 140 as indicated at 935 is at a strength dB 1, different from the initial application of the auxiliary field at strength dB indicated at 920. It should be noted that pulse sequence 930 is typically the same pulse sequence as pulse sequence 905, altered as necessary to accommodate the changes in the main magnetic field. The variations in main field strength to dB1and dB can coincide in location and duration within the two pulse sequences. The pulse sequence pairs may be repeated, a predetermined number of times, as they are varied appropriately to obtain two complete images. In variations, the two images may be acquired sequentially. For example, a number of pulse sequences desired to obtain a first image may be applied at a first main magnetic field, and repeated at a second main magnetic field strength to obtain a second image. In other variations, other methods for obtaining two images at two different main magnetic field strengths can be used. To generate the final contrast enhanced image, the two images can be combined as described above. It should be noted that a field-shifting magnetic field may be applied during portions of the scan other than the phase accrual portion. For example, the field-shifting magnetic field can remain on during data acquisition, or for part of the data acquisition. In further implementations, the strength of the field-shifting field applied may vary within or at different portions of the SWI pulse sequence.

The process of acquiring multiple images at differing main magnetic fields field-shifted by field-shifting coils 140 may be repeated as many times as required. For example, in some implementations, more than two images may be acquired. When more than two images are used they may be combined in any manner that can increase the relative image contrast. This may include subtracting images in pairs, then summing the subtracted images; summing all the images together; fitting the signal at each pixel location across all the images to some parametric model; or other mathematical combinations. In further implementations, the strength of the field-shifting field applied may vary within or at different portions of the SWI pulse sequence. For example, the auxiliary filed can remain on during the data acquisition, or for part of the data acquisition.

Field-shifting properties of DREMR system 100 can also be combined with other T2*-weighted MR imaging techniques. As discussed above, T2* relaxation refers to the decay of transverse magnetization caused by a combination of spin-spin relaxation and magnetic field inhomogeneity. T2* relaxation has contributions both from the T2 relaxation which is an inherent tissue property, as well as contributions from local magnetic field inhomogeneities, commonly referred to as the decay time T2'. The three relaxations are related by $1/T_2^*=1/T_2+1/T_2'$, where $T_2' \cong \gamma \Delta B_0$ where $\Delta B0$ measures the magnetic field inhomogeneity. Accordingly, T2* relaxation, as described above, can be detected with gradient-echo (GRE) imaging because transverse relaxation T2' caused by magnetic field inhomogeneities, unlike in the case of a 180° pulse at spin-echo imaging, is not eliminated by a GRE pulse.

There can be many contributions to the magnetic field inhomogeneities including inhomogeneities in the main magnetic field due to characteristics of main magnet 110, as well as magnetic susceptibility based field differences. Both of these effects scale linearly with the strength of the main magnetic field. Thus, the rate of signal decay T2', and hence T2*, may vary in different materials placed within different main magnetic fields.

One or more T2*-weighted MR images may be acquired using known T2*-weighted imaging methods, with a field-shifting magnetic field being provided by the field-shifting coils 140 for at least some of the images during all or part of the time during which T2* decay occurs in the pulse sequence. The T2* dispersion signal can then be generated by observing the variation in T2*-weighted signal at each magnetic field strength for a given material such as tissue and/or region of the image, for example. Accordingly, changes in main field strength of DREMR system 100 can be provided through variations in the field-shifting magnetic field applied by the filed-shifting coils 140. The variation of T2* dispersion signal in accordance with the main magnetic field can then be analyzed to differentiate different tissues by identifying, for example, unique patterns in the relationship between T2* and magnetic field strength or, as another example application, determine iron content within the tissues. As further example, the T2* dispersion analysis can include the identification of unique magnetic field strengths where there is a rapid increase or decrease in the T2* dispersion curve that may be a unique characteristic for a given tissue.

Figure 10:
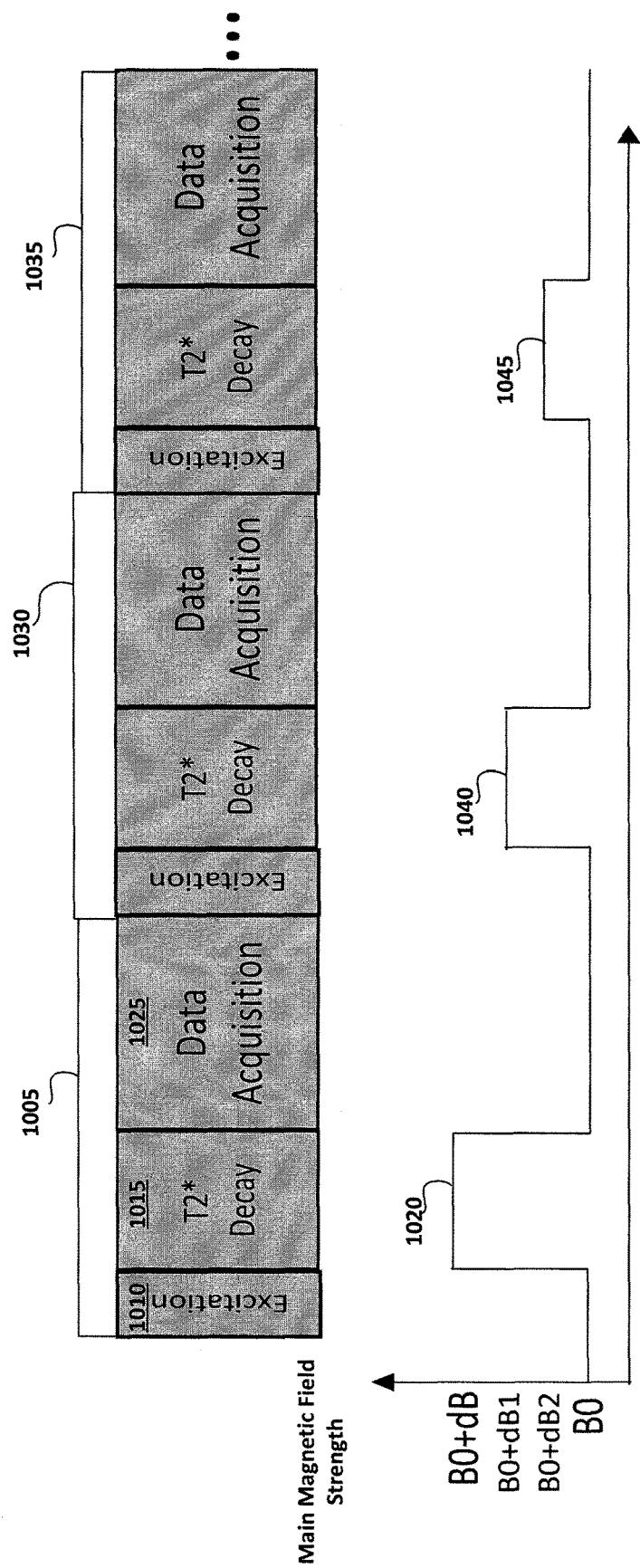
FIG. 10 shows an example pulse sequence for augmented MR signal acquisition using the example DREMR system of FIG. 1 based on T2* based imaging.

Referring to FIG. 10, an example method of generating a T2* dispersion signal using DREMR system 100 is illustrated. Excitation is achieved, through application of an RF pulse by the RF coils 130, at excitation portion 1010 of a T2* pulse sequence 1005 for acquiring T2* signal. At the T2* decay portion 1015, of the T2* pulse sequence 1005, a field-shifting magnetic field is applied by the field-shifting coils 140 as indicated at 1020. Next, the data acquisition portion 1025 of the T2* pulse sequence allows acquisition of the MR signals. The process is then repeated, as indicated at the second T2* pulse sequence 1030 and third T2* pulse sequence 1035. However, during the second pulse sequence 1030, and the third pulse sequence 1035 the field-shifting magnetic field applied by the field-shifting coils 140 as indicated at 1040 and 1045 respectively is at strengths differing from the initial application of the field-shifting field indicated at 1020. Specifically, at 1040, the main magnetic field strength has been shifted to B0+dB1and at 1045, the main filed strength has been shifted to B0+dB2. The repetition may occur an additional predetermined number of times. It should be noted that a field-shifting magnetic field may be applied during portions of the pulse sequence other than the T2* decay portion. In some implementations, the strength and/or duration of the field-shifting field applied may vary within or at different portions of the T2* pulse sequence. For example, the field-shifting filed can remain on during or part of the data acquisition portion of a pulse sequence. Although this example discusses obtaining and comparing signals associated with a single pulse sequence repeated at different main magnetic field strengths, the same process can be applied to entire images or portions or regions of images acquired in a similar manner, using different main field strengths.

Figure 11:
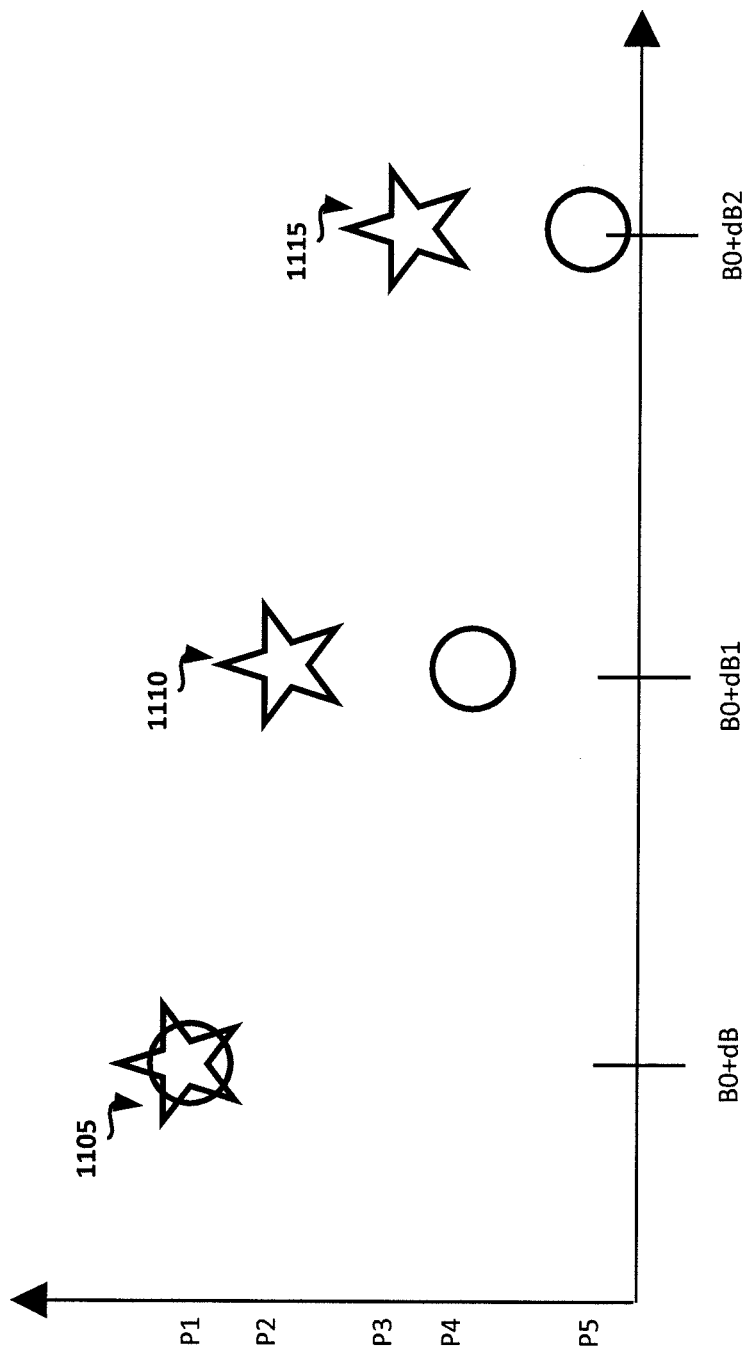
FIG. 11 shows a conceptual illustration of T2* signal separation from 2 materials.

Once the multitude of signals or images are acquired at different main field strengths, they may be compared to determine changes in T2* dispersion. Referring to FIG. 11, a conceptual illustration of how T2* signals from 2 materials, indicated by a circle and a star, which could be the same (P1) at one field strength (B0+dB indicated at 1105 and corresponding to signals acquired using T2* pulse 1005 of FIG. 10) can be differentiated by repeating MR signal acquisition at shifted main magnetic fields. At magnetic field strength B0+dB1, indicated at 1110 and corresponding to signals acquired using T2* pulse 1030 of FIG. 10, the T2* signals for the two materials are now different (P2 and P4). At magnetic field strength B0+dB2, indicated at 1115 and corresponding to signals acquired using T2* pulse 1035 of FIG. 10, the T2* signals for the two materials or tissues are further differentiated (P3 and P5). Based on these differentiations, the type of material can be determined. For example, the differentiation may simply indicate a specific magnetic field strength (which may be different from the unshifted main field strength of the MRI system) at which there is the largest difference in T2* values between two tissues and at which T2* based imaging would be preferably performed. Alternatively, the dispersion patterns for any set of tissues may suggest specific data processing to increase T2* based signal differentiation from the tissues. This could include fitting the measured T2* dispersion points to a specific model (shape of variation), subtraction or other linear combinations of signals or images at specific magnetic field strengths or other image combination methods.

As discussed above, T2' component of T2*, and accordingly, T2* varies with the applied magnetic field strength. For most materials or tissues, the expected variation of T2* with respect to main magnetic field strength is linear. Specifically, the T2* change caused by an increase in the main magnetic field strength may be balanced by a T2* change caused by a decrease in the field strength by the same amount. For some materials, in particular those containing iron, the variation of T2* with respect to the field strength can be non-linear. The DREMR system 100 can be used to take advantage of this non-linearity to perform enhanced iron or BOLD imaging. T2* weighted images, both with and without main field perturbations, can be acquired. Such pairs of images may be performed such that they differ in regions where the T2* response to field variations is non-linear. For example regions containing iron-based compounds may show changes in contrast.

To implement a differential acquisition, a first acquisition may be performed where no main field perturbation is applied. In a second acquisition of the same MR image, the main field strength can be varied in a manner which can alter the image contrast for materials having a non-linear response to the field variation. As an example, the main field may be changed in one direction during a T2* decay portion of a T2* pulse sequence, and may be changed in an equal but opposite direction, and for equivalent duration, for another portion of the T2*decay. For materials having a non-linear response to main magnetic field variations, the change in T2* dispersion when the main magnetic field increases by a predetermined amount may not be balanced by the change in T2* dispersion when the main magnetic field decreases by an equal amount and duration. This may be in contrast to tissues or materials that vary linearly with respect to changes in the main magnetic field where the change in T2* dispersion can be the same when the main magnetic field is perturbed up and down by the same amount and duration.

Figure 12:
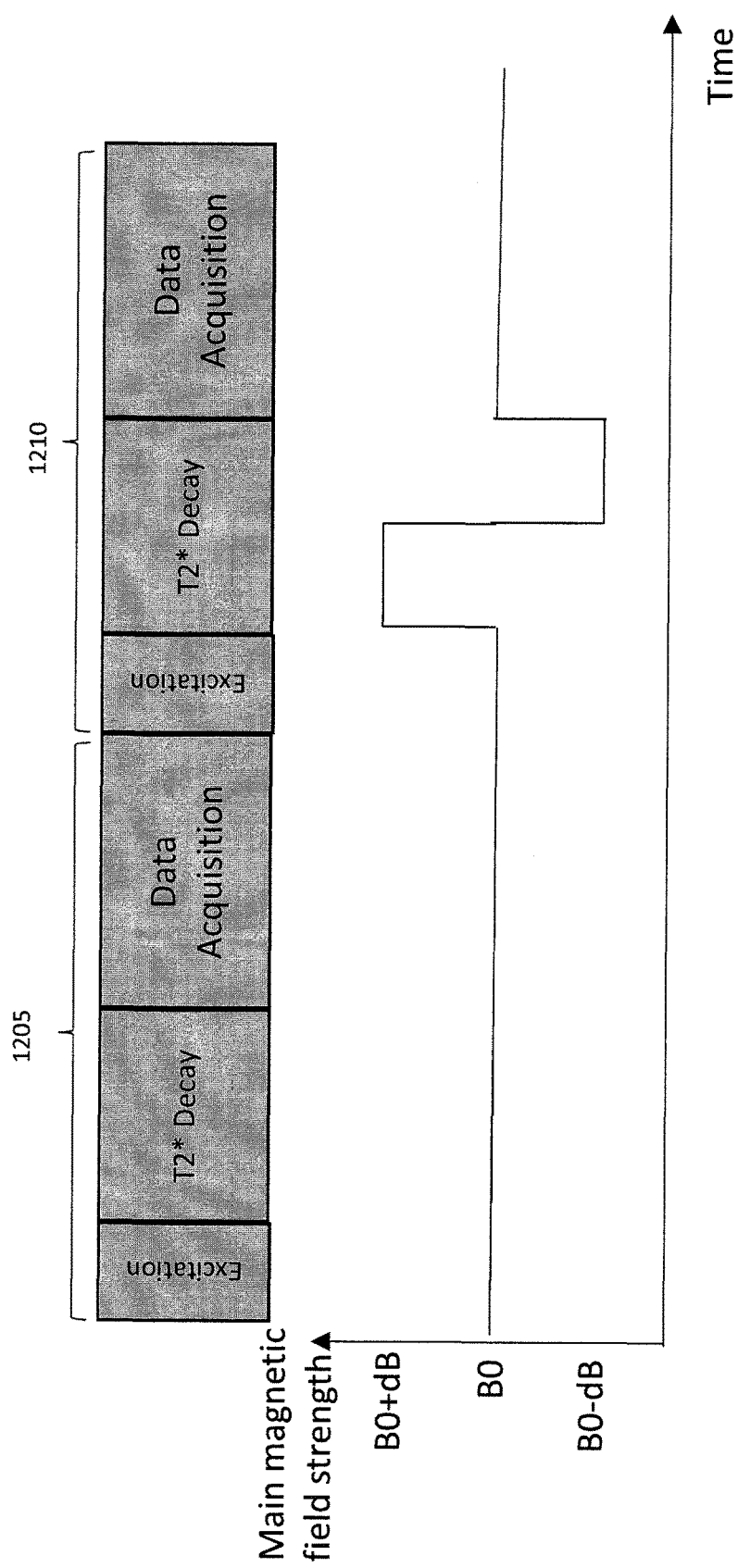
FIG. 12 shows an example pulse sequence for augmented MR signal acquisition using the example DREMR system of FIG. 1 based on T2* based imaging.

Referring to FIG. 12, an example of a method for performing Iron or BOLD imaging using a DREMR system 100 is illustrated. In this figure pulse sequence 1205 is used to perform a T2*-weighted acquisition at main field strength B0, without any main field perturbations. Following the MR signal acquisition based on the pulse sequence 1205, the same pulse sequence is repeated at 1210. This time, however, the main field strength B0 is increased by dB for a period of time during which T2* decay is occurring, through an application of a field-shifting magnetic field by filed-shifting coils 140. Following the increase, the main field strength is decreased by the same amount dB, again through the application of an auxiliary magnetic field by field-shifting coils 140 for an equivalent duration. Subsequently, the MR data is acquired. It should be noted that although in this example, the main magnetic field strength is first increased, and then decreased by the same amount for an equal duration, many different ways of perturbing the main magnetic field during the T2* decay portion of a pulse sequence is possible as long as the perturbations occur in a manner which can alter the image contrast for materials having a non-linear response to field variations. For example, the main magnetic field may be altered in a manner such that the alterations are balanced. There are various methods for achieving balanced alterations. For example, in some variations a series of increases and decreases of equivalent amounts in the main magnetic field strength may be applied during the T2* decay portion of the pulse sequence. The main magnetic field may be increased first, then decreased by an equivalent amount and duration, increased back up, and decreased again by an equivalent amount and duration to the last increase. Each increase-decrease pair may be by a different amount and duration. Moreover, the order of increase and decrease may change, and pairs may not be located immediately adjacent to each other. Although this example discusses obtaining signals associated with a single pulse sequence repeated at different main magnetic field strengths, it is to be understood that a similar process can be applied to the acquisition and analysis of two or more images.

Field-shifting properties of DREMR system 100 can also be combined with MR spectroscopy. As discussed above, MR spectroscopy is a method whereby MR data is acquired and processed to identify components of a substance that have different resonant frequencies. The difference in resonant frequencies may arise, for example, based on protons existing in different chemical environments within a compound or within different compounds within a material such as a tissue. MR spectroscopy is often used to analyze substances that are at a very low concentration and thus generate very low MR signals. Accordingly, a distribution of peaks at different frequencies are developed from MR signals to identify different tissues or materials. However, MR signals acquired also include significant noise. The noise is generally uniformly distributed across all frequencies. Due to the low concentration and low signal of compounds in tissues or materials, it can be difficult to identify peaks above random noise associated with signal acquisition. To counter the low signal-to-noise ratio that is typical in these measurements, often MR signal acquisition is repeated and averaged together as a method of averaging down white noise.

The DREMR system 100 can allow performing improved MR spectroscopy through acquisition of multiple MR signals at different main magnetic field strengths. The relative separation of peaks may be proportional to the main magnetic field strength. Moreover, the size of the peaks may also weakly depend on the main magnetic field strength. On the other hand, random noise signals do not typically vary, in a determinate manner, with changes in the main magnetic field strength. Accordingly, MR signal acquisitions can be repeated using the DREMR system 100, with at least some of the repeats being made at differing main magnetic field strengths. Any peaks present in the acquired MR signal may thus move by known amounts based on the known shift in the main magnetic field. Accordingly, the acquired MR signals may be processed to identify peaks that have shifted by the predicted amounts making it possible to improve the detection of desired signal peaks.

Figure 13:
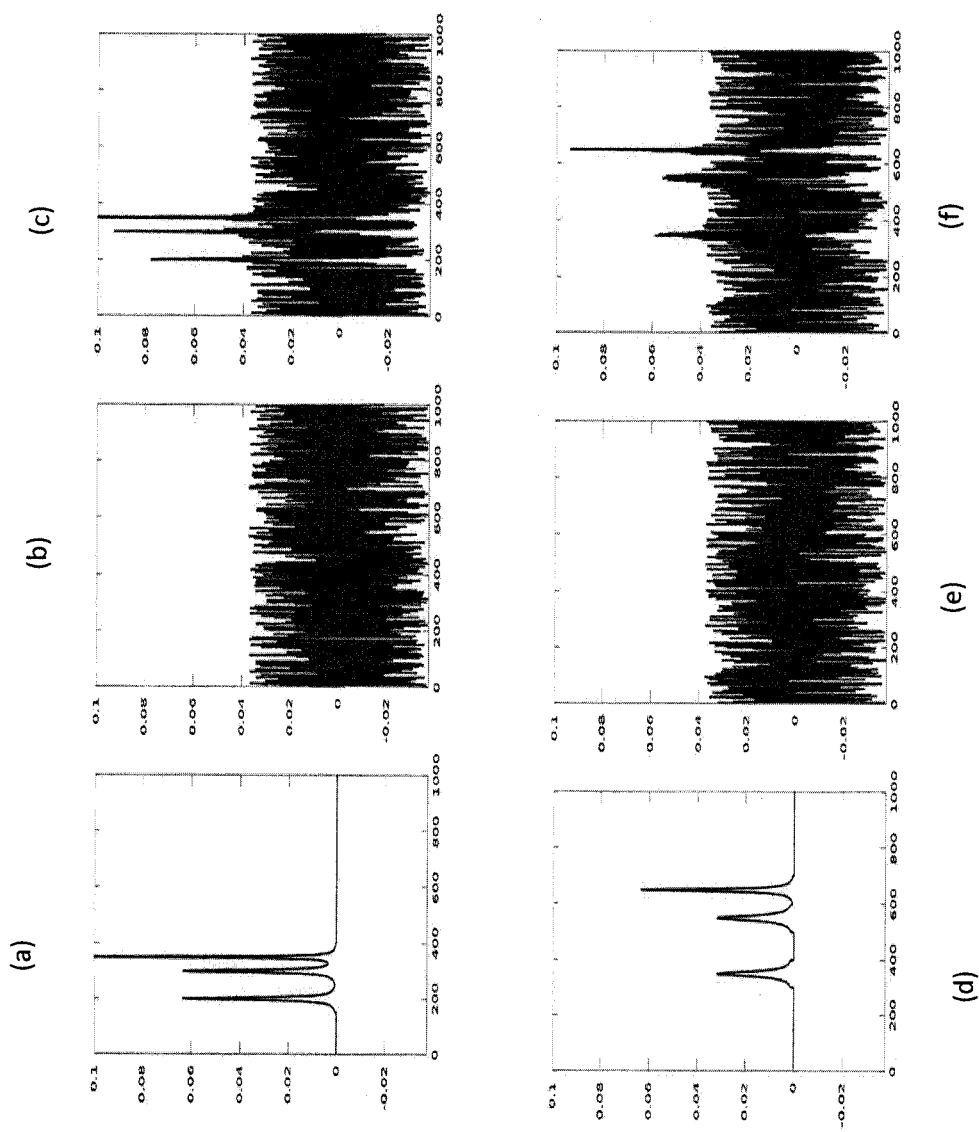
FIG. 13 shows idealized results of performing augmented MR signal acquisition using the example DREMR system 100 of FIG. 1.

Referring to FIG. 13, an example method for performing MR spectroscopy using the DREMR system 100 is illustrated. FIG. 13(a) illustrates 3 possible ideal signal peaks which are located at different frequencies for a given main field B0. FIG. 13(b) illustrates a characteristic random noise that is uniformly distributed over all frequencies and FIG. 13(c) illustrates a combined signal resulting from the combination of the ideal peaks with the characteristic noise. FIG. 13(c) is indicative of the type of signal that would be acquired by DREMR system 100.

Continuing with the figure, FIG. 13(d) illustrates the 3 possible ideal signal peaks corresponding to the three signal peaks of FIG. 13(a). However, in FIG. 13(d), the main magnetic field provided for acquisition of the MR signals is increased by a field-shifting magnetic field with a strength dB. Accordingly, the position and amplitude of all 3 peaks are scaled relative to the 3 peaks of FIG. 13(a), in proportion to the change of the main field strength from B0 to B0+dB. For example if B0+dB is equivalent to a main field with a strength of 2*B0, the position of the peaks in FIG. 13(d) may be scaled in frequency by a multiple of 2 relative to the peaks in FIG. 13(a). FIG. 13(e) illustrates a characteristic random noise acquired at the augmented main magnetic field strength B0+dB. As shown, the noise may not change with respect to the change in the main field strength in a predictable and systematic way. Finally, FIG. 13(f) illustrates a combined signal resulting from the combination of the ideal peaks of FIG. 13(d) with the characteristic noise of FIG. 13(e). FIG. 13(f) is indicative of the type of signal that would be acquired by DREMR system 100.

Correlating the peak movements with a change in the strength of the main magnetic field may help filter out randomly distributed noise which is invariant with respect to changes in the main magnetic field strength. For example, to determine whether a peak is present in a pair of MR signals acquired at different main magnetic field strengths, the peak's expected locations, which would be different at different main magnetic field strengths, can be checked in both MR signals. A peak can be assumed to be present when it is found in the expected locations in both images, the locations determined in part on the basis of the difference in main field strengths.

Although only two acquisitions were used in this illustrative example, additional acquisitions can be performed, and spectra obtained can be used in the determination of peak presence through the correlation of peak locations in the additional MR signals. In variations, each signal acquisition at a given main magnetic field strength may also be repeated at the same magnetic field strength, and the signals thus acquired averaged to partially average out white noise as described above.

Field-shifting properties of DREMR system 100 can also be combined with MR fingerprinting. Any given tissue or material may be characterized based on a set of measured MR signal properties, referred to as the MR fingerprint of that tissue. For example, for a given tissue or material, multiple MR signal properties can be quantified on the basis of MR signals acquired for that tissue or material. Accordingly T1, T2, T2* and/or other MR signal properties can be obtained for each tissue or material based on MR signals acquired using one or more pulse sequences. These obtained set of MR signal parameters can then be used to characterize the MR scanned tissue or material.

MR signal properties can be dependent on the strength of the main magnetic field applied during signal acquisition. Accordingly, obtaining MR signal properties at multiple field strengths can add an additional dimension to the set of parameters that could be used to characterize and differentiate tissues. Accordingly, a set of MR signal properties are selected, and scans are performed with the DREMR system 100 using appropriate pulse sequences for the selected MR properties to obtain the selected MR signal properties. The acquisition of the MR signal properties are then repeated with different main magnetic field strengths. The change in main magnetic field strength is accomplished by applying an auxiliary magnetic field using the field-shifting coils 140. The field-shifting magnetic field can be can be specific to each MR signal acquisition and applied in a manner that make MR signal measurements sensitive to changes in the main magnetic field strength. Some of these techniques, for example for the acquisition of T2* property, are discussed above. As a further illustrative example, to obtain a T1 measurement, well-established MR acquisition methods for mapping the T1 relaxation parameter can be used. The acquisition can be repeated with an auxiliary field applied by field-shifting coils 140 during the inversion time (TI) portion of the pulse sequence.

Figure 14:
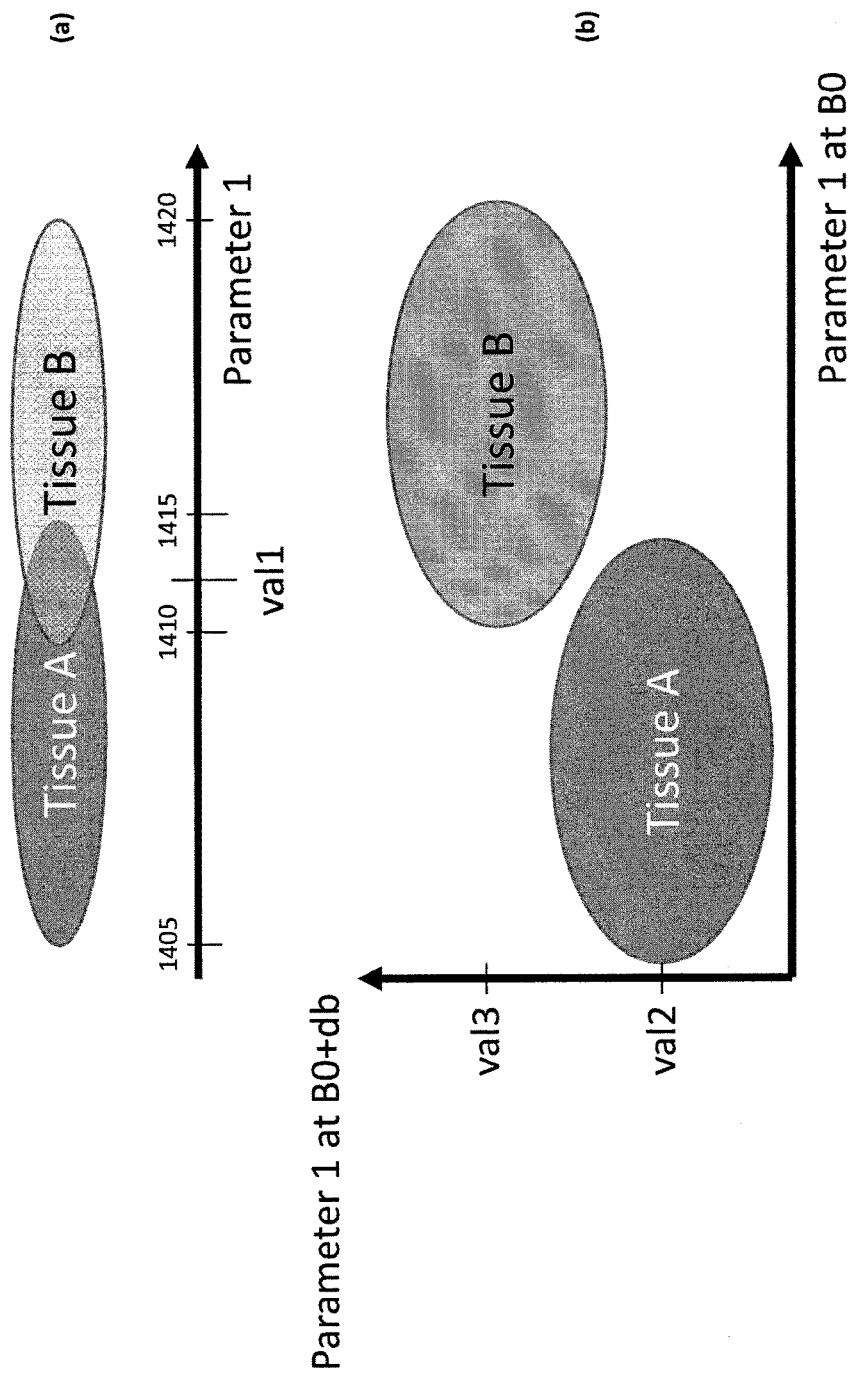
FIG. 14 shows a simplified example of the effects of magnetic field strength changes to MR fingerprinting results.

FIG. 14 provides a simplified illustrated example of how the addition of magnetic field strength changes can enhance MR fingerprinting. FIG. 14(a) shows a distribution of values of one MR signal property, Parameter1, for two different tissue types at main magnetic field strength B0 along the x-Axis. The y-axis has been added for illustrative convenience, and does not represent any values. According to FIG. 14(a), if the measured MR signal property Parameter1 falls between 1405 and 1410, the tissue can be identified as Tissue A. If the measured MR signal property Parameter1 falls between 1415 and 1420, on the other hand, the tissue can be identified as Tissue B. The distribution of values for the two tissues overlap. Accordingly, for a tissue of interest, after scanning the tissue, if a MR signal Parameter value of "Val1" was obtained, it would not be possible to uniquely identify what tissue type that value represented.

Continuing with the figure, FIG. 14(b) illustrates, along the x-axis, a distribution of values of one MR signal property ("Parameter 1") for two different tissue types at main magnetic field strength B0 along the x-Axis, as in FIG. 14(a). However, in this case, the y-Axis represents the acquisition distribution of values of the same MR signal property, Parameter1, for the same two tissue types at main magnetic field strength B0+dB. It can be noted that when the MR signal property Parameter1 varies with respect to changes in the main magnetic field strength, the measured MR signal property value for Parameter1 for a given tissue will also change. Accordingly, the tissue of interest discussed above that had a Parameter1 value of Val1 at magnetic field strength B0, may have a Parameter1 value of Val2 or Val3 at magnetic-field strength B0+dB. Accordingly, if a tissue provides the measurement Val1 when measuring Parameter1 at B0 and Val2 when measuring Parameter1 B0 +dB, the tissue may be uniquely identified. Similarly, a measurement of Val3 for Parameter1 at B0+db may uniquely identify the tissue of interest as being a different tissue. Note that this example is for 1 measured parameter whereas in practice more than one parameters may be used, at least some which being magnetic field dependent. The unique separation of tissue types may be resolved across multiple parameter dimensions, some of which will include one or more measurements at varying magnetic field strengths.

The addition of field-dependent contrast agents to tissues being scanned by DREMR system 100 pulse sequences can further enhance the detection of traumatic brain injury (TBI), which is quite difficult to image using traditional MRI techniques. The contrast agents used typically have a relaxation profile that varies with the main field strength, both in their bound and unbound state.

In some cases, an opening in the normally closed blood brain barrier (BBB) may allow albumin and fibrinogen to enter (normally inaccessible) brain tissue, and can be a specific cause of brain inflammation. Selectively imaging these molecules would enable imaging sites of albumin to and fibrinogen penetration in the brain, which may be used to identify areas of brain trauma. To determine sites of increased albumin/fibrinogen in the brain, the patient can be injected with a bolus of (appropriate) contrast agent and imaged with a field varying gradient echo scan. By varying the field strength, molecular contrast can be achieved. It would be advantageous to observe the quantity of albumin/fibrin in the brain, as well as to observe the time course of the spread of albumin/fibrin in a manner similar to current perfusion imaging.

The above-described embodiments are intended to be examples and alterations and modifications may be effected thereto, by those of skill in the art, without departing from the scope which is defined solely by the claims appended hereto. For example, methods, systems and embodiments discussed can be varied and combined, in full or in part.

We claim:

1. A method of acquiring magnetic resonance (MR) signals at a delta-relaxation enhanced MR imaging (DREMR) system comprising:
generating a main magnetic field with a strength of B0;
generating an initial pulse sequence for acquiring T2* weighted MR imaging signals;
varying the main magnetic field strength to a strength of B0+dB during at least one portion of the initial pulse sequence;
acquiring a first image based on the initial pulse sequence;
generating a repeat pulse sequence for acquiring T2* weighted MR imaging signals, each portion of the repeat pulse sequence corresponding to the at least one portion of the initial pulse sequence and varying the main magnetic field strength to a strength of B0+dB1; and
acquiring a second image based on the repeat pulse sequence,
wherein the initial pulse sequence is the pulse sequence for acquiring T2* weighted MR imaging signals, wherein the initial pulse sequence includes at least one T2* decay portion and wherein the portion of the pulse sequence during which the main magnetic field strength is varied to B0+dB is at least a portion of the at least one T2* decay portion, and wherein the main magnetic field strength that is varied to B0+dB1 is different from B0+dB during the repeat pulse sequence;
generating a T2* dispersion signal based on a variation in the T2* weighted MR imaging signals at each main magnetic field strength B0+dB and B0+dB1; and identifying the main magnetic field strengths wherein there is a change in the T2* dispersion signal to differentiate tissues.

2. The method of claim 1 wherein the initial pulse sequence is the pulse sequence for acquiring T2* weighted MR imaging signals, wherein the initial pulse sequence includes a T2* decay portion, and wherein the portion of the pulse sequence during which the main magnetic field strength is varied to B0+dB is at least a portion of the at least one T2* decay portion, the method further comprising:
for each T2* decay portion of the initial pulse sequence where the main magnetic field strength is varied to B0+dB, further varying the main magnetic field strength during that T2* decay portion in a manner that balances variation of the main magnetic field strength to B0+dB; and wherein for each portion of the repeat pulse sequence corresponding to the at least one portion of the initial pulse sequence where the main magnetic field strength is varied in a balanced manner, further varying the main magnetic field strength in a manner that balances variation of the main magnetic field strength to B0+dB1.

3. The method of claim 1 further comprising:
repeating image acquisition at various time points; and
calculating a spread of contrast agent based on the acquired images.

4. A method of acquiring magnetic resonance (MR) signals at a delta-relaxation enhanced MR imaging (DREMR) system comprising:
generating a main magnetic field with a strength of B0;
generating an initial pulse sequence for acquiring T2* weighted MR imaging signals;
varying the main magnetic field strength to a strength of B0+dB during at least one portion of the initial pulse sequence;
acquiring a first image based on the initial pulse sequence;
generating a repeat pulse sequence for acquiring T2* weighted MR imaging signals, each portion of the repeat pulse sequence corresponding to the at least one portion of the initial pulse sequence and varying the main magnetic field strength to a strength of B0+dB1; and
acquiring a second image based on the repeat pulse sequence,
wherein the initial pulse sequence is the pulse sequence for acquiring T2* weighted MR imaging signals, wherein the initial pulse sequence includes at least one T2* decay portion and wherein the portion of the pulse sequence during which the main magnetic field strength is varied to B0+dB is at least a portion of the at least one T2* decay portion, and wherein the main magnetic field strength that is varied to B0+dB1 is different from B0+dB during the repeat pulse sequence;

generating a T2* dispersion signal based on a variation in the T2* weighted MR imaging signals at each main magnetic field strength B0+dB and B0+dB1; and identifying pattern relationships between the T2* dispersion signal and each main magnetic field strength B0+dB and B0+dB1 to differentiate tissues.

5. The method of claim 4 wherein the initial pulse sequence is the pulse sequence for acquiring T2* weighted MR imaging signals, wherein the initial pulse sequence includes a T2* decay portion, and wherein the portion of the pulse sequence during which the main magnetic field strength is varied to B0+dB is at least a portion of the at least one T2* decay portion, the method further comprising:

for each T2* decay portion of the initial pulse sequence where the main magnetic field strength is varied to B0+dB, further varying the main magnetic field strength during that T2* decay portion in a manner that balances variation of the main magnetic field strength to B0+dB; and wherein for each portion of the repeat pulse sequence corresponding to the at least one portion of the initial pulse sequence where the main magnetic field strength is varied in a balanced manner, further varying the main magnetic field strength in a manner that balances variation of the main magnetic field strength to B0+dB1.

6. A delta-relaxation enhanced magnetic resonance (MR) imaging (DREMR) system comprising:
a main magnet operating to generate a main magnetic field with a strength of B0;
radio frequency coils having a transmit aspect and gradient coils operating to generate an initial pulse sequence for acquiring at least one of: T2*-weighted MR imaging signals; susceptibility weighted imaging (SWI) signals; and saturation imaging signals;
field-shifting magnets operating to vary the main magnetic field strength to a strength of B0+dB during at least one portion of the initial pulse sequence;
the radio frequency coils having a receive aspect operating to acquire a first image based on the initial pulse sequence;
the radio frequency coils transmit aspect and gradient coils further operating to generate a repeat pulse sequence for acquiring T2* weighted MR imaging signals, each portion of the repeat pulse sequence corresponding to the at least one portion of the initial pulse sequence;
the radio frequency coils receive aspect further operating to acquire a second image based on the repeat pulse sequence,
wherein the initial pulse sequence is the pulse sequence for acquiring T2* weighted MR imaging signals, wherein the initial pulse sequence includes at least one T2* decay portion and wherein the portion of the pulse sequence during which the main magnetic field strength is varied to B0+dB is at least a portion of the at least one T2* decay portion, and wherein the main magnetic field strength that is varied to B0+dB1 is different from B0 +dB during the repeat pulse sequence; and
a data processing system operating to generate a T2* dispersion signal based on a variation in the T2* weighted MR imaging signals at each main magnetic field strength B0+dB and B0+dB1 and identify the main magnetic field strengths wherein there is a change in the T2* dispersion signal to differentiate tissues.

7. A delta-relaxation enhanced magnetic resonance (MR) imaging (DREMR) system comprising:

a main magnet operating to generate a main magnetic field with a strength of B0;
gradient coils;
radio frequency coils having a transmit aspect, the transmit aspect of the radio frequency coils and the gradient coils operating to generate an initial pulse sequence for acquiring MR spectroscopy signals;
field-shifting magnets operating to vary the main magnetic field strength to a strength of B0+dB during at least one portion of the initial pulse sequence;
the radio frequency coils having a receive aspect, the receive aspect of the radio frequency coils operating to acquire a first spectroscopy signal based on the initial pulse sequence;
the transmit aspect of the radio frequency coils and the gradient coils operating to generate a repeat pulse sequence for acquiring MR spectroscopy signals, each portion of the repeat pulse sequence corresponding to the at least one portion of the initial pulse sequence;
the field-shifting magnets operating to vary the main magnetic field strength to a strength of B0+dB during at least one portion of the repeat pulse sequence;
the receive aspects of the radio frequency coils operating to acquire a second spectroscopy signal based on the repeat pulse sequence, wherein the initial pulse sequence is the pulse sequence for acquiring T2* weighted MR spectroscopic signals, wherein the initial pulse sequence includes at least one T2* decay portion and wherein the portion of the pulse sequence during which the main magnetic field strength is varied to B0+dB is at least a portion of the at least one T2* decay portion, and wherein the main magnetic field strength that is varied to B0+dB1 is different from B0+dB during the repeat pulse sequence; and
a data processing system operating to identify peaks from the first and the second spectroscopy signals and correlating the identified peaks, and to generate a T2* dispersion signal based on a variation in the T2* weighted MR spectroscopic signals at each main magnetic field strength B0+dB and B0+dB1 and identify the main magnetic field strengths wherein there is a change in the T2* dispersion signal to differentiate tissues.

8. A delta-relaxation enhanced magnetic resonance (MR) imaging (DREMR) system comprising:
a main magnet operating to generate a main magnetic field with a strength of B0;
gradient coils;
radio frequency coils having a transmit aspect, the transmit aspect of the radio frequency coils and the gradient coils operating to generate an initial pulse sequence for acquiring MR signals for fingerprinting;
the radio frequency coils having a receive aspect, the receive aspect of the radio frequency coils operating to acquire a first image based on the initial pulse sequence;
the transmit aspect of the radio frequency coils and the gradient coils operating to generate a repeat pulse sequence for acquiring MR fingerprinting signals, each portion of the repeat pulse sequence corresponding to the initial pulse sequence;
field-shifting magnets operating to vary the main magnetic field strength to a strength of B0+dB during at least one portion of the repeat pulse sequence;
the receive aspect of the radio frequency coils operating to acquire a second image based on the repeat pulse sequence, wherein the initial pulse sequence is the pulse sequence for acquiring T2* weighted MR signals, wherein the initial pulse sequence includes at least one T2* decay portion and wherein the portion of the pulse sequence during which the main magnetic field strength is varied to B0+dB is at least a portion of the at least one T2* decay portion, and wherein the main magnetic field strength that is varied to B0+dB1 is different from B0+dB during the repeat pulse sequence; and a data processing system operating to identify tissue type based on the at least one MR signal property obtained based on the first and the second images, and to generate a T2* dispersion signal based on a variation in the T2* weighted MR signals at each main magnetic field strength B0+dB and B0+dB1 and identify the main magnetic field strengths wherein there is a change in the T2* dispersion signal to differentiate tissues.

\* \* \* \* \*